(12) United States Patent
Santana Milian et al.

(10) Patent No.: US 11,510,965 B2
(45) Date of Patent: Nov. 29, 2022

(54) VESICLES COMPRISING EPIDERMAL GROWTH FACTOR AND COMPOSITIONS THEREOF

(71) Applicants: Centro de Ingeniería Genética y Biotecnología, Havana (CU); Consejo Superior de Investigaciones Científicas, Madrid (ES)

(72) Inventors: Héctor Jesús Santana Milian, Havana (CU); Leonor Ventosa Rull, Barcelona (ES); Eduardo Martínez Díaz, Havana (CU); Jorge Amador Berlanga Acosta, Havana (CU); Ingrid Cabrera Puig, Mayabeque (CU); Jaume Veciana Miró, Barcelona (ES)

(73) Assignee: Centro de Ingeniería Genética y Biotecnología, Havana (CU)

( * ) Notice: Subject to any disclaimer, the term of this patent is extended or adjusted under 35 U.S.C. 154(b) by 0 days.

(21) Appl. No.: 15/664,548

(22) Filed: Jul. 31, 2017

(65) Prior Publication Data
US 2018/0015145 A1    Jan. 18, 2018

Related U.S. Application Data

(62) Division of application No. 14/418,511, filed as application No. PCT/CU2013/000004 on Aug. 2, 2013, now Pat. No. 9,717,776.

(30) Foreign Application Priority Data
Aug. 2, 2012   (CU) .................................. 2012-0112

(51) Int. Cl.
```
A61K 38/18    (2006.01)
A61K 8/41     (2006.01)
A61K 8/63     (2006.01)
A61K 8/64     (2006.01)
A61Q 19/08    (2006.01)
A61K 9/00     (2006.01)
A61K 9/127    (2006.01)
A61K 8/14     (2006.01)
A61K 47/18    (2017.01)
A61K 47/28    (2006.01)
A61L 26/00    (2006.01)
```

(52) U.S. Cl.
CPC ............ *A61K 38/1808* (2013.01); *A61K 8/14* (2013.01); *A61K 8/416* (2013.01); *A61K 8/63* (2013.01); *A61K 8/64* (2013.01); *A61K 9/0014* (2013.01); *A61K 9/127* (2013.01); *A61K 9/1271* (2013.01); *A61K 9/1277* (2013.01); *A61L 26/0066* (2013.01); *A61Q 19/08* (2013.01); *A61K 47/186* (2013.01); *A61K 47/28* (2013.01); *A61K 2800/805* (2013.01); *A61L 2300/414* (2013.01)

(58) Field of Classification Search
None
See application file for complete search history.

(56) References Cited

U.S. PATENT DOCUMENTS

| | | | |
|---|---|---|---|
| 4,944,948 A | 7/1990 | Uster et al. | |
| 5,618,544 A | 4/1997 | Brown | |
| 9,579,261 B2 | 2/2017 | Hwang et al. | |
| 2002/0081324 A1 | 6/2002 | Twine | |
| 2007/0259971 A1 | 11/2007 | Ventosa et al. | |
| 2012/0107412 A1 | 5/2012 | Gammelsaeter et al. | |

FOREIGN PATENT DOCUMENTS

| | | |
|---|---|---|
| WO | WO9009782 A1 | 9/1990 |
| WO | WO2006079889 A1 | 8/2006 |
| WO | WO2007065464 A1 | 6/2007 |
| WO | WO2007073704 A1 | 7/2007 |

OTHER PUBLICATIONS

Letizia et al., J. Phys. Chem. B, 111:898-908, 2007.*
Mire-Sluis et al., "Quantitative cell line based bioassays for human cytokines," Journal of Immunological Methods, vol. 187, pp. 191-199, 1995.
Vazquez et al., "Radio and Enzyme Immunoassays for Human Epidermal Growth Factor with Mouse Monoclonal Antibodies," Biotechnologia aplicado, vol. 7, No. 1, pp. 42-51, 1998.
Li et al., "Polyethylene glycol-coated liposomes for oral delivery of recombinant human epidermal growth factor," International Journal of Pharmaceutics, vol. 258, pp. 11-19, 2003.
Keung et al., "Applications, and Efficient Large-Scale Production, of Recombinant Human Epidermal Growth Factor," Biotechnology and Genetic Engineering Reviews, vol. 18, pp. 51-71, 2001.
Brown et al., "Acceleration of Tensile Strength of Incisions Treated with EGF and TGF-B," Ann. Surg., vol. 208, No. 6, pp. 788-794, 1988.
Yerushalmi et al., "Molecular and Cellular Studies of Hyaluronic Acid-Modified Liposomes as Bioadhesive Carriers for Topical Drug Delivery in Wound Healing," Archives of Biochemistry and Biophysics, vol. 313, No. 2, pp. 267-273, 1994.
Elizondo et al., "Influence of the Preparation Route on the Supramolecular Organization of Lipids in a Vesicular System," Journal of the American Chemical Society (JACS), vol. 134, pp. 1918-1921, 2012.

(Continued)

*Primary Examiner* — Marianne P Allen
(74) *Attorney, Agent, or Firm* — Hoffmann and Baron, LLP

(57) ABSTRACT

The invention relates to vesicles comprising Epidermal Growth Factor (EGF), a cationic surfactant and cholesterol or derivatives thereof. The invention also discloses a procedure for their preparation, based on compressed fluid technology (CFs). The vesicles of the invention are useful in the manufacture of drugs and cosmetics and in tissue engineering.

23 Claims, 6 Drawing Sheets

(56) References Cited

OTHER PUBLICATIONS

Valdes et al., "Improving the expression of Human Epidermal Growth Factor in *Saccharomyces cerevisiae* by manipulating culture conditions," Biotecnologia Aplicada, vol. 26, pp. 34-38, 2009.
Degim et al., "Evaluation of chitosan gel containing liposome-loaded epidermal growth factor on burn wound healing," International Wound Journal, vol. 8, No. 4, pp. 343-354, 2011.
Lee et al., "Preparation and Characterization of Mono-PEGylated Epidermal Growth Factor: Evaluation of in Vitro Biologic Activity," Pharmaceutical Research, vol. 19, No. 6, pp. 845-851, Jun. 2002.
Svoboda et al., "Structural characterization and biological activity of recombinant human epidermal growth factor proteins with different N-terminal sequences," Biochimica et Biophica Acta, vol. 1206, pp. 35-41, 1994.
Koivisto et al., "HaCaT keratinocyte migration is dependent on epidermal growth factor receptor signaling and glycogen synthase kinase-3α," Experimental Cell Research, vol. 312, pp. 2791-2805, 2006.
MacDonald et al., "Small-volume extrusion apparatus for preparation of large, unilamellar vesicles," Biochimica et Biophica Acta, vol. 1061, pp. 297-303, 1991.
Elizondo et al., "Liposomes and Other Vesicular Systems: Structural Characteristics, Methods of Preparation, and Use in Nanomedicine," Progress in Molecular Biology and Translational Science, vol. 104, pp. 1-52, 2011.
Andersen et al., "The Role of Decorated SDS Micelles in Sub-CMC Protein Denaturation and Association," J. Mol. Biol., vol. 391, pp. 207-226, 2009.
Alves et al., Local delivery of EGF-liposome mediated bone modeling in orthodontic tooth movement by increasing RANKL expression, Life Sciences, vol. 85, pp. 693-699, 2009.
Jung et al., Particle design using supercritical fluids: Literature and patent survey, Journal of Supercritical Fluids, vol. 20, pp. 179-219, 2001.
Haedo et al., "Oral human recombinent epidermal growth factor in the treatment of patients with duodenal ulcer," Rev. Esp. Enf. Digest, vol. 88, No. 6, pp. 409-413, 1996.
Shin et al., "Synthesis and Biological Activity of N-Terminal-Truncated Derivatives of Human Epidermal Growth Factor (h-EGF)," Peptides, vol. 16, No. 2, pp. 205-210, 1995.
Bennett et al., "Growth Factors and Wound Healing: Part II. Role in Normal and Chronic Wound Healing," The American Journal of Surgery, vol. 166, pp. 74-81, 1993.
Hasegawa et al., "Epidermal Growth Factor Suppresses in Vitro Senescence in the Ability of Human Umbilical Vein Endothelial Cells to Proliferate, but not in the Ability to Produce Prostacyclin," Mechanisms of Ageing and Development, vol. 66, pp. 107-114, 1992.
Blessing et al., "Different Strategies for Formation of PEGylated EGF-Conjugated PEI/DNA Complexes for Targeted Gene Delivery," Bioconjugate Chem, vol. 12, pp. 529-537, 2001.
Woods et al., "Materials processing in supercritical carbon dioxide: surfactants, polymers and biomaterials," Journals of Materials Chemistry, vol. 14, pp. 1663-1678, 2004.
Yoon et al., "Expression of Recombinant Epidermal Growth Factor in *E. coli*," Biotechnol. Bioprocess Eng. vol. 2, pp. 86-89, 1997.
Cooper, A., "Porous Materials and Supercritical Fluids", Adv. Mater., vol. 15, No. 13, pp. 1049-1059, 2003.
Holmes et al., "Supercritical Fluid Synthesis of Metal and Semiconductor Nanomaterials," Chem. Eur. J. vol. 9, pp. 2144-2150, 2003.
Agrawal et al., "6-Mercaptopurine and Daunorubicin Double Drug Liposomes—Preparation, Drug-Drug Interaction and Characterization," Journal of Liposome Research, vol. 15, pp. 141-155, 2005.
Cooper, A., "Recent Developments in Materials Synthesis and Processing Using Supercritical CO2," Advanced Materials, vol. 13, No. 14, pp. 1111-1114, 2001.
Girdler et al. "The Effect of Epidermal Growth Factor Mouthwash on Cytotoxic-Induced Oral Ulceration," Am. J Clin Oncol (CCT), vol. 18 (5), pp. 403-406, 1995.
Cano-Sarabia et al., "Preparation of Uniform Rich Cholesterol Unilamellar Nanovesicles Using CO2-Expanded Solvents," Langmuir, vol. 24, pp. 2433-2437, 2008.
Majima, K., "Effect of Epidermal Growth Factor upon Morphological Changes of Human Lens Epithelial Cells," Ophthalmologica, vol. 212, pp. 250-256, 1998.
Lee et al., "N-Terminal Site-Specific Mono-PEGylation of Epidermal Growth Factor," Pharmaceutical Research, vol. 20, No. 5, pp. 818-825, 2003.
Spectroscopy et al. "Investigation of Denaturation of Human Serum Albumin under Action of Cethyltrimethylammonium Bromide," Laser Physics, vol. 21, No. 1, pp. 239-244, 2011.
Calnan et al., "Potency and stability of C terminal truncated human epidermal growth factor," Gut BMJ Journals, vol. 47, pp. 622-627, 2000.
Lahti et al., "Engineered epidermal growth factor mutants with faster binding on-rates correlate with enhanced receptor activation," FEBS Letters, vol. 585, pp. 1135-1139, 2011.
Ristori et al., "Structural Characterization of Cationic Liposomes Loaded with Sugar-Based Carboranes," Biophysical Journal, vol. 88, pp. 535-547, 2005.
Kikuchi et al., "Efficient Gene Transfer to EGF Receptor Overexpressing Cancer Cells by Means of EGF-Labeled Cationic Liposomes," Biochemical And Biophysical Research Communications vol. 227, Article No. 1566, pp. 666-671, 1996.
Li et al., "Multivesicular Liposomes for Oral Delivery of Recombinant Human Epidermal Growth Factor," Archives of Pharmacal Research, vol. 28, No. 8, pp. 988-994, 2005.
Razis et al., "Expression of Recombinant Human Epidermal Growth Factor in *Escherichia coli* and Characterization of its Biological Activity," Appl Biochem Biotechnol vol. 144, pp. 249-261, 2008.
Hudson et al., "Contributions of the Epidermal Growth Factor Receptor to Keratinocyte Motility," Microscopy Research and Technique, vol. 43, pp. 444-455, 1998.
Liang et al., "Anti-apoptotic role of EGF in HaCaT keratinocytes via a PPAR B-dependent mechanism," Wound Repair and Regeneration, vol. 16, pp. 691-698, 2008.
Alemdaroglu et al., "Investigation of epidermal growth factor containing liposome formulation effects on burn wound healing," Journal of Biomedical Materials Research Part A, pp. 271-283, 2007.
Vaiana et al., "Epidermal Growth Factor: Layered Silicate Nanocomposites for Tissue Regeneration," Biomacromolecules, vol. 12, pp. 3139-3146, 2011.
Kirby et al., "Dehydration-Rehydration Vesicles: a Simple Method for High Yield Drug Entrapment in Liposomes," Nat. Biotechnology, vol. 2, pp. 979-984, 1984.
Shiah et al., "Pseudomonas Exotoxin A—Epidermal Growth Factor (EGF) Mutant Chimeric Protein as an Indicator for Identifying Amino Acid Residues Important in EGF-Receptor Interaction," The Journal of Biological Chemistry, vol. 267, No. 33, pp. 24024-24040, 1992.
Saddi et al., "Epidermal Growth Factor in Liposomes May Enhance Osteoclast Recruitment during Tooth Movement in Rats," Angle Orthodontist, vol. 78, No. 4, pp. 604-609, 2008.
Carrion et al., "The Influence of Ionic Strength and Lipid Bilayer Charge on the Stability of Liposomes," Journal of Colloid and Interface Science, vol. 164, pp. 78-87, (1994).
Akin et al., "The Determination of Molecular Weights of Biologically Active Proteins by Cetyltrimethylammonium Bromide-Polyacrylamide Gel Electrophoresis," Analytical Biochemistry, vol. 145, pp. 170-176, 1985.
Smith et al., "Measurement of Protein Using Bicinchoninic Acid," Analytical Biochemistry, vol. 150, pp. 76-85, 1985.
Valdes et al., "Physiological study in *Saccharomyces cerevisiae* for overproduction of a homogeneous human epidermal growth factor molecule," Biotecnologia Aplicada, vol. 26, No. 2, pp. 166-167, 2009.

(56) References Cited

OTHER PUBLICATIONS

Lanio et al., "Humoral Immune Response Against Epidermal Growth Factor Encapsulated in Dehydration Rehydration Vesicles of Different Phospholipid Composition," Journal of Liposome Research, vol. 18, pp. 1-19, 2008.

* cited by examiner

A

B

VESICLES COMPRISING EPIDERMAL GROWTH FACTOR AND COMPOSITIONS THEREOF

CROSS-REFERENCE TO RELATED APPLICATIONS

This application is a division of U.S. application Ser. No. 14/418,511, filed Jan. 30, 2015, which is a U.S. National Phase of, and Applicant claims priority from, International Patent Application Number PCT/CU2013/000004, filed Aug. 2, 2013, which claims priority from CU 2012-0112, filed Aug. 2, 2012, each of which is incorporated herein by reference in their entireties.

FIELD OF THE INVENTION

The present invention falls within the fields of human and veterinary medicine, cosmetics and tissue engineering, particularly in the field of vesicular type release systems comprising Epidermal Growth Factor (EGF) in their composition. The vesicles of the invention have improved therapeutic efficacy in relation to free EGF.

BACKGROUND OF THE INVENTION

Drug delivery systems based on vesicular systems, usually liposomes, composed of amphiphilic molecules that incorporate a therapeutically active substance, constitute one of the most widely used systems in the pharmaceutical sector, because they can provide increased stability to the active principle, increase its permeability through biological membranes, and allow slow release of the active ingredient without the need of repeated administrations.

EGF is one of the main growth factors that stimulate cell proliferation and motility during tissue regeneration. It also helps maintain tissue hemostasis through the regulation of epithelial cell proliferation and migration. Furthermore, EGF induces angiogenesis, which provides nutritional support to the tissue (Hudson and McCawley, *Microsc. Res. Tech.* 1998, 43: 444-455; Koivisto et al., *Exp. Cell Res.* 2006, 312: 2791-2805; Liang et al., *Wound Repair Regen.* 2008, 16: 691-698). This growth factor has multiple applications in the pharmaceutical field (Wong et al., *Biotechnol. Genet. Eng. Rev.* 2001, 18: 51-71; Girdler et al., *Am. J. Clin. Oncol.* 1995, 18: 403-406; Haedo et al., *Rev. Esp. Enferm. Dig.* 1996, 88: 409-413; Majima, *Ophthalmologica* 1998, 212:250-256); in cosmetics (Hasegawa and Yamamoto, *Mech. Ageing. Dev.* 1992, 66:107-114, Patent No. U.S. Pat. No. 5,618,544) and in tissue engineering (Christopher et al., *Biomacromolecules* 2011, 12: 3139-3146).

EGF formulations using different liposome systems have been developed. Some examples are EGF integration in unilamellar liposomes comprising phosphatidylglycerol (PG), phosphatidylcholine (PC) and cholesterol (Brown et al., *Ann. Surg.* 1988, 208: 788-794). The inclusion of EGF has also been reported in multilamellar liposomes comprising PC, cholesterol and hyaluronic acid (Yerushalmi, et al., *Arch. Biochem. Biophys.* 1994, 313: 267-273); or comprising cholesterol and dipalmitoylphosphatidylcholine (DPPC) (Alemdaroğlu et al., *J. Biomed. Mater. Res. A* 2008, 85A: 271-283; Degim et al., *Int. Wound. J.* 2011, 8: 343-354). Another class of liposomes that have been reported are the multivesicular ones comprising dioleoylphosphatidylcholine (DOPC), dimyristoyl phosphatidylglycerol (DMPG), cholesterol and triolein (Li et al., *Arch. Pharm. Res.* 2005, 28: 988-994).

On the other hand, liposomes that comprise cationic lipids conjugated to EGF have been reported (Kikuchi et al., *Biochem. Biophys. Res. Commun.* 1996, 227: 666-671); polyethylene glycol (PEG) coated liposomes, which also comprise cholesterol and dioleoylphosphatidylethanolamine (DOPE) in combination with PC or DPPC (Li et al., *Int. J. Pharm.* 2003, 258: 11-19). Liposomes comprising DPPC and lysophosphatidylcholine (LPC) have also been reported (Saddi et al., *The Angle Orthodontist* 2008, 78: 604-609; Alves et al., *Life Sci.* 2009, 85: 693-699).

EGF formulations using liposomal systems have also been protected by patents, such as the one disclosing the gel composition of EGF/liposome and methods comprising EGF entrapment in liposomes containing neutral and negatively-charged phospholipids (Patent No. U.S. Pat. No. 4,944,948); the gel composition of liposomes and methods that use negatively-charged liposomes and EGF, and include negatively charged lipids, such as: PG, PC and cholesterol (International Patent Application No. WO 9009782). Another patent application relates to the topical application of EGF in liposomes to prevent diabetic foot amputation, and liposomes comprising PC and sodium deoxycholate are used. This patent application is restricted to the use of any type of liposomes/niosomes of EGF for the topical treatment of grades IV and V chronic ischemic lesions of diabetic foot (International Patent Application No. WO 2007/073704). In the prior art, EGF integration in vesicular systems constituted by cholesterol and cationic surfactants has not been found.

Traditional methods for obtaining liposomes, such as thin-film evaporation (Agrawal et al., *J. Liposome Res.* 2005, 15: 141-155), dehydration-rehydration (Kirby and Gregoriadis, *Nat. Biotechnol.* 1984, 2: 979-984), freeze-thawing (Ristori et al., *Biophys. J.* 2005, 88: 535-547) and extrusion (MacDonald et al., *Biochim. Biophys. Acta* 1991, 1061: 297-303) have certain drawbacks. Some of these drawbacks are associated to the use of large amounts of solvents, which are difficult to eliminate afterwards, or with the high temperatures required by some of these methods, limiting their use to thermally stable substances. On the other hand, the size and nanostructuring of the material are difficult to control and these methods have low reproducibility during the scale-up (multi-stage processes). Another problem with liposome preparations is their poor stability.

Processing of materials with compressed fluids (CFs), or dense gases, both in liquid or supercritical state, as solvents, have aroused great expectancy at academic and industrial levels, for preparing micro- or nanostructured materials such as: particulate materials, vesicular systems, composite particles, structured surfaces, etc., with greater structural homogeneity than that achieved by conventional processing (Holmes et al., *Chem. Eur. J.* 2003, 9: 2144-2150; Cooper, *Adv. Mater.* 2001, 13: 1111-1114; Cooper, *Adv. Mater.* 2003, 15: 1049-1059 and Woods et al., *J. Mater. Chem.* 2004, 14: 1663-1678). A CF or a dense gas is a substance that at normal conditions of pressure and temperature exists as gas but increasing the pressure can be converted into liquids or supercritical fluids, and be used as solvent media for chemical and material processing.

The most frequently used CF is carbon dioxide ($CO_2$), classified as green solvent, because it is non-toxic, non-flammable, easy to remove, leaves no residues in the particles, is inexpensive and easy to recover. Since the early '90s, a series of methodologies that use CFs for preparing finely divided materials, with micro-, sub-micro and nanoscopic particle sizes, have been developed (Jung and Perrut, *J. Supercrit. Fluid,* 2001, 20: 179-219). The solvating power of CFs may be modified by temperature and composition changes, as in the case of conventional liquid solvents, and also by pressure changes, which are transmitted much faster within solutions. Therefore, these precipitation methods have in common the possibility of achieving very high grades of supersaturation in very short time intervals, promoting nucleation over crystal growth and thereby obtaining micro- or nanoparticles with very narrow size distributions, controlled internal structure and supramolecular organization.

One of the processes to obtain micro- or nanostructured materials with CFs is the method called DELOS-SUSP—Depressurization of an Expanded Liquid Organic Solution-Suspension— (International Patent Application No. WO 2006/079889; Patent No. EP 1843836; Cano-Sarabia et al., *Langmuir* 2008, 24: 2433-2437), which is based on depressurization of an organic solution previously expanded by a CF, generating either a micro- or a nanodisperse system by said depressurization. In this process, the CF acts as co-solvent, being completely miscible, under certain conditions of pressure and temperature, with the organic solution of the solute to be stabilized as micro- or nanodisperse system. Said stabilization is achieved in the presence of additives in the medium, usually aqueous, on which depressurization of the expanded solution is carried out. Additives may be emulsifiers, ionic and non-ionic detergents, surface agents, colloid stabilizers and protectors. Using this method micro- and/or nanodisperse systems, such as liposomes, emulsions or suspensions, can be obtained. The liposomes or vesicles are composed of cholesterol and other membrane agents, such as phospholipids and surfactants, and their preparation requires dissolution of cholesterol and/or other lipids in the expanded organic solution and its depressurization in an aqueous surfactant solution.

For the possible incorporation of actives in vesicles or liposomes by DELOS-SUSP, and to generate the corresponding vesicles, it is required to dissolve the active ingredient in the initial expanded solution, or in the aqueous solution, in which depressurization of said expanded solution is carried out and in both cases, this dissolution must be carried out in the presence of lipids, detergents or surface active agents.

Among cationic surfactants, those of quaternary ammonium type (QUATs) have been widely used in pharmaceuticals and cosmetics. In the pharmaceutical field, they have been used by topical, ophthalmic, oral, buccal and nasal routes. Previously, the preparation of cholesterol:cetyltrimethylammonium bromide (CTAB) nanovesicles using DELOS-SUSP technology has been reported. One example of the incorporation of water soluble compounds by this technology is described in the reference "Liposomes and other vesicular systems: structural characteristics, methods of preparation, and use in nanomedicine" (*Progress in Molecular Biology and Translational Science, Elsevier,* 2011, vol. 104, pp. 1-52), where cholesterol:CTAB vesicles are used as vehicle for encapsulation and administration of the antibiotic gentamicin. It must be emphasized that reported gentamicin encapsulations are very low (<2%). This type of vehicle has never been used to incorporate proteins. It is known that ionic detergents are agents that cause protein denaturation (Akin et al., *Anal. Biochem.* 1985, 145: 170-176; Andersen et al., *J. Mol. Biol.* 2009, 391: 207-226). Denaturation of human serum albumin after CTAB addition has been recently demonstrated by Raman spectroscopy (Vlasova and Saletsky, *Laser Phys.* 2011, 21: 239-244). Denaturation, as a rule, is accompanied by the loss of functional properties of the protein.

Due to all the above mentioned reasons, it is still of interest to achieve new release systems of EGF, easy to standardize, with high homogeneity at the structural level and in its physico-chemical properties, that improve the pharmaceutical and pharmacological properties and/or increase the therapeutic activity of EGF.

BRIEF DESCRIPTION OF THE INVENTION

The present invention relates to vesicles, as drug delivery system, which comprise EGF, a cationic surfactant and cholesterol or one of its derivatives and have greater therapeutic effectiveness than those previously described.

The present invention also relates to a process for the preparation of said vesicles comprising EGF, a cationic surfactant and cholesterol or derivatives thereof, that includes: a) preparation of an aqueous solution of EGF and a cationic surfactant, b) the dissolution of cholesterol or one of its derivatives in an organic solvent expanded with a CF, c) the synthesis of the vesicles by depressurization of the solution resulting from stage b) on the solution resulting from stage a).

A pharmaceutical composition characterized by comprising vesicles that include EGF, a cationic surfactant and cholesterol, or derivatives thereof, and at least one pharmaceutically acceptable excipient is also an object of the invention. Another object of the invention is the use of said vesicles for the manufacture of medicaments and cosmetics.

The pharmaceutical compositions of this invention, which contain EGF vesicles with other components, are useful as drugs to accelerate the healing process of diabetic foot ulcers and other complex wounds, such as: venous ulcers, decubitus ulcers, burns, among others; to repair the anterior chamber structures in damaged eyes, in systemic mucositis and in all the diseases of the gastrointestinal tract that involve the need to regenerate mucosa and submucosa. In particular, it has been found that these vesicles have significantly greater therapeutic effectiveness for healing diabetic foot ulcers and venous ulcers than those described in the prior art.

The invention also relates to a cosmetic product characterized by comprising vesicles of EGF, a cationic surfactant and cholesterol or derivatives thereof.

DETAILED DESCRIPTION OF THE INVENTION

Figure 1:
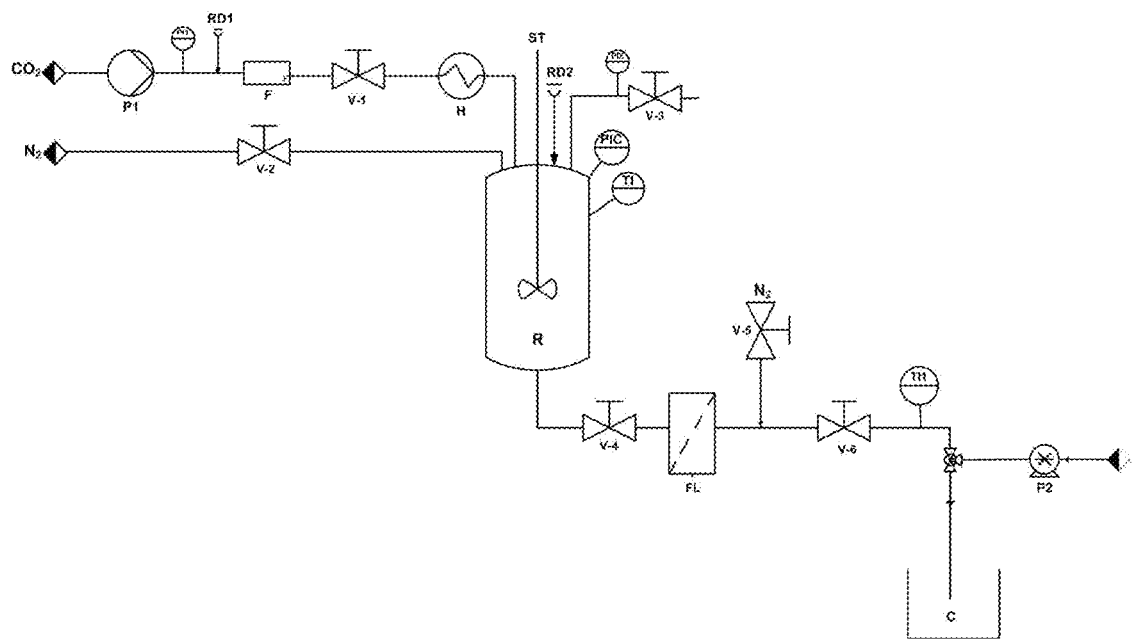
FIG. 1. Schematic representation of an equipment for obtaining vesicles comprising EGF, a cationic surfactant and cholesterol or a cholesterol-derivative where: C, Collector; H, Heat exchanger; P, Pump; R, Reactor; V, Valve; RD, Rupture disc; ST, Stirrer; FL, Filter; TI, Temperature indicator; PI, Pressure indicator; PIC, Pressure indicator controller; F, Flow meter.

The present invention provides vesicles that are characterized by comprising epidermal growth factor (EGF), a cationic surfactant and cholesterol or derivatives thereof. In an embodiment of the invention, the cationic surfactant is of quaternary ammonium type.

In the context of this invention the term "EGF" refers to any variant of the EGF molecules that maintains their biological activity; for example, C-terminal truncated molecules (Calnan et al., *Gut* 2000, 47: 622-627); or molecules truncated at the N-terminal (Svodoca et. al., *Biochim. Biophys. Acta* 1994, 1206: 35-41; Shin et al., *Peptides* 1995, 16: 205-210). EGF can be obtained by recombinant DNA technology using yeasts like *Saccharomyces* (Valdés et al., *Biotecnol. Apl.* 2009, 26: 1-9) or *Pichia pastoris* (*Research Journal of International Studies* 2009, 10: 36-46); using bacteria, such as *Escherichia coli* (Yoon et al., *Biotechnol. Bioprocess Eng.* 1997, 2: 86-89; Abdull Razis et al., *Appl. Biochem. Biotechnol.* 2008, 144: 249-261); or by methods of chemical synthesis (Shin et al., *Peptides* 1995, 16: 205-210). The EGF object of the invention also comprises whichever variant obtained by the previously described methods, after being modified by any procedure of the prior art, such as: amino acid substitution (Shiah et al., *J. Biol. Chem.* 1992, 267: 24034-24040; Lahti et al., *FEBS Lett.* 2011, 585: 1135-1139; International Patent Application No. WO 2007/065464), and polyethylene glycol conjugation (Thomas et al., *Bioconjugate Chem.* 2001, 12: 529-537; Lee et al., *Pharm. Res.* 2003, 20: 818-825), or any other method of chemical or genetic modification.

The term "cationic surfactant" refers to those surfactants with at least one positive charge in the molecule and also includes the combination of one or more cationic surfactants. For example, according to the present invention, cationic surfactants of the tertiary amine salt type, quaternary ammonium salt and alkyl ammonium in saturated and unsaturated heterocycles can be used.

In the invention, the term "quaternary ammonium type (QUATs) cationic surfactant" refers to quaternary ammonium salts in which at least one nitrogen substituent is a long chain. Compounds such as CTAB, cetrimide and BKC or their mixture are included among QUATs. In a preferred embodiment of the present invention, the cationic surfactant used is a surfactant acceptable in pharmaceutics. The QUATs as well as the rest of the cationic surfactants can be obtained from commercially available sources, with pharmaceutical and cosmetic qualities.

In the present invention, the term "vesicles" refers to colloidal microparticles and nanoparticles, which are between 25 nm and 5 μm and are formed by one or more bilayers of amphiphilic molecules that contain an aqueous phase.

In one embodiment of the invention, the vesicles have a molar ratio of cationic surfactant to cholesterol (or derivatives thereof) in the range of 10 M:1 M to 1 M:5 M and a molar ratio of EGF to cholesterol (or its derivatives thereof) which is in the range of 0.5 μM:1 M to 100 μM:1 M.

The term "derivatives" of cholesterol, in the present invention, refers to molecules of the steroids family, generally obtained from the cholesterol precursor molecule and having lipophilic character.

In one embodiment of the invention, the vesicles comprising EGF are characterized by having unilamellar structure and approximate mean size between 25 and 500 nm, preferably between 50 and 300 nm. In a particular embodiment, the invention refers to vesicles in which EGF is incorporated into the vesicle bilayer. The approximate size and morphology of the vesicles are evaluated by Cryo-TEM and the distribution of vesicle size is characterized by DLS.

Surprisingly, the vesicles of the invention show significant increase in the biological potency of EGF (measured in vitro) compared to free EGF and EGF in cholesterol:DPPC liposomes. Moreover, these vesicles are capable of protecting EGF against protease attack, a very important characteristic for achieving adequate bioavailability of EGF at the site of action; therefore, increasing its therapeutic effectiveness.

In the present invention, for the first time, EGF vesicles that improve some of the pharmaceutical and pharmacological properties of this growth factor, such as its potency and stability, have been synthesized. It has been demonstrated that the degree of incorporation of EGF in the structure of the vesicles remains stable for at least one year. Additionally, they enable to increase of permeability through biological membranes.

The vesicles of the invention have the additional advantage of antimicrobial and antifungal effect, which is desirable in compositions used in the treatment of complex wounds and other lesions susceptible of EGF treatment.

In an embodiment of the invention, the vesicles comprising EGF are obtained by CF technology. In a particular embodiment, the CF technology that is used to obtain the vesicles includes a process comprising a) preparation of an aqueous solution of EGF and a cationic surfactant, b) dissolution of cholesterol or derivatives thereof in an organic solvent expanded with a CF, and c) vesicle synthesis by depressurization of the solution resulting from stage b) on the solutions resulting from stage a). In a preferred embodiment, the cationic surfactant used in stage a) is of quaternary ammonium-type.

The invention also provides a process for preparing vesicles that comprise EGF, a cationic surfactant and cholesterol or its derivatives characterized by comprising a) the preparation of an aqueous solution of EGF and a cationic surfactant, b) dissolution of cholesterol or derivatives thereof in an organic solvent expanded with a CF, and c) vesicle synthesis by depressurization of the resulting solution in stage b) on the solution resulting in stage a). In one embodiment of the invention, the above described process includes a cationic surfactant of quaternary ammonium type.

In one embodiment of the invention, the organic solvent in stage b) of the above mentioned process is a solvent selected from the group formed by monohydric alcohols, such as: ethanol, methanol, 1-propanolol, 2-propanolol, 1-butanol, 1-hexanol, 1-octanol and trifluoroethanol; polyhydric alcohols, such as: propylene glycol, PEG 400 and 1,3-propanediol; ketones, such as acetone, methyl ethyl ketone and methyl isobutyl ketone; ethylenediamine, acetonitrile, ethyl acetate and mixtures thereof. In any case, whatever is the nature of the organic solvent, the lipid component has to be soluble in it and further, said solvent has to necessarily be miscible in CF and water. Moreover, the selected organic solvent must have relatively low toxicity.

The relative concentration of EGF and surfactant in the initial buffer solution and the cholesterol concentration in the organic solvent are determined by the desired ratio of cholesterol:cationic surfactant:EGF in the final vesicle. In general, the cholesterol: cationic surfactant:EGF ratio can influence the physico-chemical and biological properties of the different vesicles obtained.

In another embodiment of the invention, the CF used in the process described before is a component selected between $CO_2$, ethane, propane, hydrochlorofluorocarbons (eg., CFC-22), and hydrofluorocarbons (eg., HFC-134A). Preferably, the CF in stage b) is $CO_2$, considered an ecological solvent, because it is non-toxic, non-flammable, non-corrosive, is not harmful for the environment and moreover, is very abundant in nature.

In one embodiment of the invention, the process for EGF vesicle preparation is performed in an apparatus, as the one shown in FIG. 1. It consists of a high-pressure reactor (R) to which a solution of cholesterol in ethanol at concentration ($C_1$) is added at atmospheric pressure and working temperature (T=Tw). In a second stage, compressed $CO_2$ is added until the working pressure (P=Pw) is reached, producing volumetric expansion of the solution to a molar fraction $X_{CO2}$. The addition is done through valve V-1 using pump P1, keeping the rest of the valves closed. The system is maintained at pressure $P_w$ and temperature $T_w$, during a specified time, to ensure complete homogenization and thermal balance. After this time, V-4 is opened to connect reactor R to filter FL, which has previously been pressurized with $N_2$ to $P_w$ keeping the rest of the valves closed. Opening V-6 allows depressurization of the volumetrically expanded solution on an aqueous EGF solution at concentration ($C_2$) and surfactant at concentration ($C_3$) pumped through P2. In this final stage, a stream of $N_2$, added through V-2 at $P_w$, is used as plunger to push down the expanded solution and to maintain constant pressure within the reactor during the depressurization stage. The presence of filter FL allows collecting any precipitate that may have formed during the process. The vesicles formed are collected in container C and subsequently stored in glass bottles at 4° C. Once depressurization is finished, V-6 and V-2 are closed and depressurization of the equipment proceeds by reopening V-6.

In one embodiment of the invention, the relationship between the amount of CF and organic solvent corresponds to a CF molar fraction of approximately 0.3 to 0.95; preferably from 0.5 to 0.8. In one particular embodiment, the dissolution of cholesterol (or derivatives thereof) in a CF is performed in a reactor at a pressure $P_w$ of approximately 1 to 30 MPa, and a $T_w$ of approximately 10 to 70° C. Preferably the approximate temperature of the reactor is between 10 and 50° C.

In the process of the invention, EGF is dissolved in an aqueous solution containing a cationic surfactant, the concentration of which is above its critical micellar concentration.

Surprisingly, the cholesterol:QUATs:EGF vesicles, synthesized using the process described above, have yields of EGF vesicle incorporation very close to 100%, which are significantly higher than those expected for the incorporation of any water-soluble molecule, taking into account the results formerly reported for gentamicin. These yields in cholesterol:QUATs:EGF vesicles are also notably higher than those obtained for the incorporation of other proteins with structural properties similar to EGF, as the water-soluble protein bovine serum albumin (BSA). This occurs even when the formerly described DELOS-SUSP procedure is used for said BSA incorporation, as only an incorporation yield of 42% is obtained.

Furthermore, and also in a surprising way, these yields of EGF incorporation into cholesterol:QUATs vesicles are clearly greater than those obtained for cholesterol:DPPC:EGF vesicles, even if the DELOS-SUSP process is used to prepare them.

Another aspect of the present invention is a pharmaceutical composition comprising vesicles comprising EGF, a cationic surfactant and cholesterol or derivatives thereof and at least one pharmaceutically acceptable excipient. The pharmaceutically acceptable excipient or excipients, which form part of the pharmaceutical composition of the present invention, can enhance the vesicle activity. Alternatively, they can help to the handling and processing of the composition of the present invention. The EGF vesicles of the present invention may be formulated in several pharmaceutical forms, such as: injectable, spray, gels, viscous solutions, creams, ointments, transdermal patches, depots, inhaled formulations and others known to those skilled in this technical field.

Various excipients can be mixed during the synthesis of the vesicles of this invention or after it to form a suitable material for the above mentioned dosage forms. Generally, excipients; such as solubilizers or solvents, surfactants, pH modifiers, antioxidants, diluents, matrix systems, complexing agents, viscosity enhancers, dispersants, humectants, colorants, flavorings, preservatives, permeability enhancers and others; can be used for usual purposes and in typical quantities without affecting the characteristics of the compositions of the present invention, as known by those skilled in this technical field (Remington's Pharmaceutical Sciences (1995)). Additional examples of excipients that may be used in pharmaceutical formulations of EGF vesicles can be found in the *Handbook of Pharmaceutical Excipients (6th edition)*.

In an embodiment of the present invention, the pharmaceutical composition is a controlled or sustained release form. Forms of sustained or controlled release usually include matrix systems, ion exchange resins, or individual barriers to control the diffusion of the EGF vesicles.

In one embodiment of the invention, for the preparation of pharmaceutical compositions, EGF vesicles are conditioned by a process of concentration-diafiltration, using known apparatus in this technical branch. The pharmaceutical compositions of the invention may be administered by various routes, among them: systemic, intralesional, mucosal, topical, transdermal, ophthalmic, or as inhaled formulation.

In another aspect, the present invention comprises the use of vesicles of EGF, a cationic surfactant, and cholesterol or derivatives thereof in the manufacture of a medicament. In an embodiment of the invention, said medicament is intended for the treatment of diseases in which is required help in the healing and tissue regeneration processes in any mammalian species; wherein cationic surfactants, cholesterol and EGF forming said vesicles are acceptable in pharmaceutics. In a preferred embodiment, the mammal is a human.

Said medical use comprises administering an effective quantity of said vesicles to treat a disease requiring exogenous EGF administration to regulate the processes of proliferation, growth and migration of epithelial cells or to induce angiogenesis.

In general, it is considered that an effective concentration for the administration of EGF vesicles of the present invention (or the composition comprising them) would be 1.0 to 200 μg/mL EGF equivalents, preferably 5.0 to 100 μg/mL EGF equivalents per administration. The volume and frequency of administration depends on the type of lesion, its size and the administration device used, as is well known by experts skilled in the art. It may also be appropriate to administer the required dose in two, three, four or more sub-doses at the appropriate intervals during the day.

The exact dosage and frequency of administration depends on the particular condition being treated and its severity, age, weight, sex, extent of disease, and the general physical condition of the patient, as well as on any other concomitant medications administered to the individual, as it is well known by those skilled in the art. Further, it is evident that the effective daily amount may decrease or increase, depending on how the patient responds to the medication, and/or the assessment made by the doctor who prescribed the drug of the present invention. Thus, the daily effective quantities listed above are to be considered as guidelines or recommendations.

In one embodiment of the invention, the medicament manufactured with the vesicles of the invention is used for treating complex wounds of any peripheral soft tissue. In a particular embodiment, the complex wound is a diabetic foot ulcer. In another particular embodiment, the drug is used for the treatment of venous ulcers, decubitus ulcers or burns.

In another embodiment of the invention, the medicament is used to treat a disease such as adult respiratory distress syndrome. The medicament manufactured with the vesicles of the invention is also useful for the treatment of digestive tract lesions such as ulcerative colitis, duodenal ulcers and distal colitis. In another embodiment, the drug is used for the treatment of eye lesions.

A cosmetic product characterized by comprising vesicles of EGF, a cationic surfactant, and cholesterol or derivatives thereof, and at least one acceptable excipient for cosmetics or dermal pharmaceuticals is also part of the present invention. In this aspect of the invention, cationic surfactants, cholesterol (or derivatives thereof) and EGF are acceptable in pharmaceutics and cosmetics.

The EGF vesicles of the present invention can be formulated into various cosmetic or dermal pharmaceutical forms, as solids, liquids and semisolids, such as and not restricted to: injections, spray atomized liquids, gels, creams, multiple emulsions, aqueous dispersions, milks, balsams, lotions, foams, sera, ointments, transdermal patches, wipes, depots, balms, powders, bars, inhaled formulations and the like, in all cases, including the rinse and the permanence formulations.

In general, the cosmetic or dermal pharmaceutical composition of the invention may contain excipients such as, but not limited to, solubilizers or solvents, surfactants, pH modifiers, antioxidants, diluents, matrix systems, complexing agents, viscosity enhancers, dispersants, humectants, gelling polymers, thickeners, softeners, stabilizers, odor absorbents, chelating agents, plant extracts, essential oils, marine extracts, agents coming from a biofermentation process, mineral salts, cell extracts and sunfilters (photoprotective agents of organic or mineral nature, active against A and/or B ultraviolet rays), pigments or dyes, flavorings, preservatives, permeability enhancers and others, and mixtures thereof, provided that they are physically and chemically compatible with the other components of the composition of the present invention. These excipients may be used for the usual purposes and in typical amounts without affecting the characteristics of the compositions of the present invention, as known by those skilled in this technical field (Additional examples can be found described in the *CTFA Cosmetic Ingredient Handbook*, Twelfth Edition (2008)). The nature of such additional adjuvants may be synthetic or natural in origin, like for example plant extracts, or coming from a biofermentation process.

Therefore, the use of the EGF vesicles previously described for the manufacture of a cosmetic product is also an object of the present invention. In an embodiment of the invention, the cosmetic product is for preventing senescence and aging of the skin.

EXAMPLES

The following examples are shown for illustrative purposes and should not be considered as limitations to the invention.

Example 1. Synthesis of Cholesterol:DPPC:EGF Vesicles Using Compressed Fluid Technology Firstly, a solution of 12 mg of cholesterol and 24 mg of DPPC in 1.2 mL of ethanol is introduced into a high pressure reactor of 6 mL volume, at atmospheric pressure and temperature (Tw=35° C.). Compressed $CO_2$ is added, causing volumetric expansion of the solution to reach a molar fraction $X_{CO2}$=0.7 and a working pressure Pw=10 MPa.

The system is left under agitation during approximately 60 minutes at 10 MPa and 35° C., to achieve full homogenization and thermal balance. Finally, the expanded organic solution is depressurized from the working pressure to atmospheric pressure, on 24 mL of an aqueous solution of EGF at the desired concentration (between 15 μM and 40 μM). In this last step, a stream of $N_2$ at 10 MPa is used as plunger to push down the volumetric expanded solution to maintain a constant working pressure in the reactor during depressurization. Subsequently, the vesicles are transferred to a hermetically sealed container and stored until use at 5±3° C.

As a result, DPPC:cholesterol (1:1) vesicles were obtained, with EGF incorporated at a concentration between 15 μM and 40 μM. The physical appearance, mean size, particle size distribution and Z-potential are shown in Table 1. The mean size, particle size distribution and Z-potential were determined by DLS.

It can be seen that the various vesicle preparations have no short-term stability problems, and have relatively small mean size and polydispersity index (PDI), which makes them attractive from the pharmaceutical viewpoint. However, the absolute Z-potential is very small (<+10 mV), well below the values that are considered to allow colloidal stability of dispersed systems, which are normally absolute values above 30 mV (Carrion et al., *J. Colloid. Interface Sci.* 1994, 164: 78-87). This characteristic indicates that the long-term stability of this vesicle system may be compromised.

TABLE 1

Physical appearance, mean particle size and Z-potential of the different variants of cholesterol:DPPC:EGF vesicles for different compositions.

| Composition (EGF:cholesterol) | Physical Appearance | Mean size (nm) (PDI)* | Z-Potential (mV) (±SD)* |
|---|---|---|---|
| 0 mM:1 M | Disperse opalescent solution | 143.2 (0.180) | +4.8 (±2.43) |
| 12.195 mM:1 M | Disperse opalescent solution | 188.3 (0.180) | +3.92 (±2.43) |
| 20.325 mM:1 M | Disperse opalescent solution | 226.4 (0.297) | +5.12 (±3.99) |
| 32.520 mM:1 M | Disperse opalescent solution | 227.3 (0.243) | +1.78 (±0.82) |

*Nano-ZS (Malvern Instruments, United Kingdom),
PDI—polydispersity index

Example 2. Synthesis of Cholesterol:CTAB:EGF Vesicles Using Compressed Fluid Technology Firstly, a solution of 76 mg of cholesterol in 2.88 mL of ethanol is introduced in a high pressure reactor that has a volume of 6 mL, at atmospheric pressure and working temperature (Tw=35° C.). Compressed $CO_2$ is added, producing volumetric expansion of the solution to reach a molar fraction $X_{CO2}$=0.7 and a working pressure Pw=10 MPa. To achieve full homogenization and thermal balance, the system is allowed to rest for about 60 minutes at 10 MPa and 35° C. Finally, the expanded organic solution is depressurized from the working pressure to atmospheric pressure, on 24 mL of a solution of CTAB in mQ water (C=2.83 mg/mL) containing EGF at the desired concentration (between 1 and 40 μM). In this last step, a stream of $N_2$ at 10 MPa is used as plunger to push the cholesterol in an ethanol solution to maintain a constant working pressure in the reactor during depressurization. Then, the vesicles are transferred to a hermetically sealed container and stored until use at 5±3° C.

The morphology of the vesicles was evaluated by cryo-TEM, according to a procedure that has been previously described (*Progress in Molecular Biology and Translational Science, Elsevier,* 2011, vol. 104, pp. 1-52).

Figure 2:
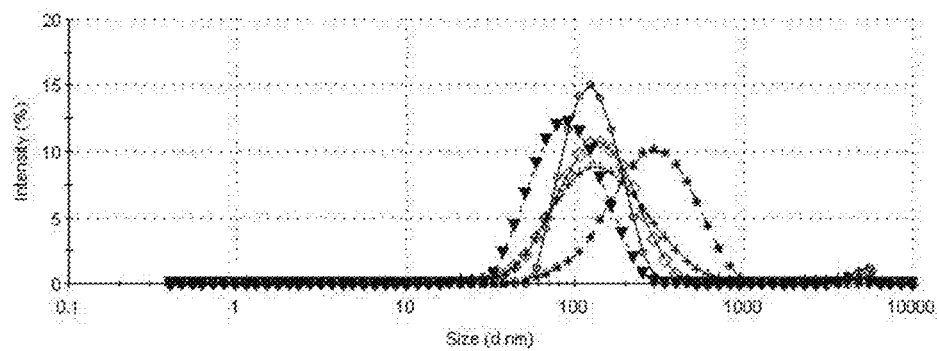
FIG. 2. Particle size distribution by dynamic light scattering (DLS) of the vesicles keeping a constant CTAB:cholesterol ratio at 1 M:1 M and varying the EGF:cholesterol ratio (0 mM:1 M (—●—), 0.684 mM:1 M (--▼--), 2.052 mM:1 M (—◆—), 3.420 mM:1 M (—■—) and 5.472 mM:1 M (- ✶ -) (A); and keeping the tetradecyl methylammonium bromide (cetrimide):cholesterol relation constant at 1 M:1 M and varying the EGF: cholesterol ratio (0 mM:1M (--▼--), 0.684 mM:1 M (—◆—), 2.052 mM:1 M (- ✶ -), 3.420 mM:1 M (—■—) and 5.472 mM:1 M (—●—) (B).
Figure 2:
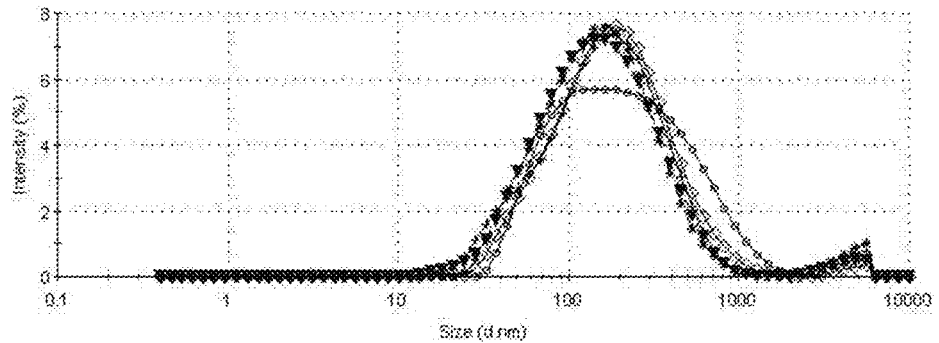
Figure 3:
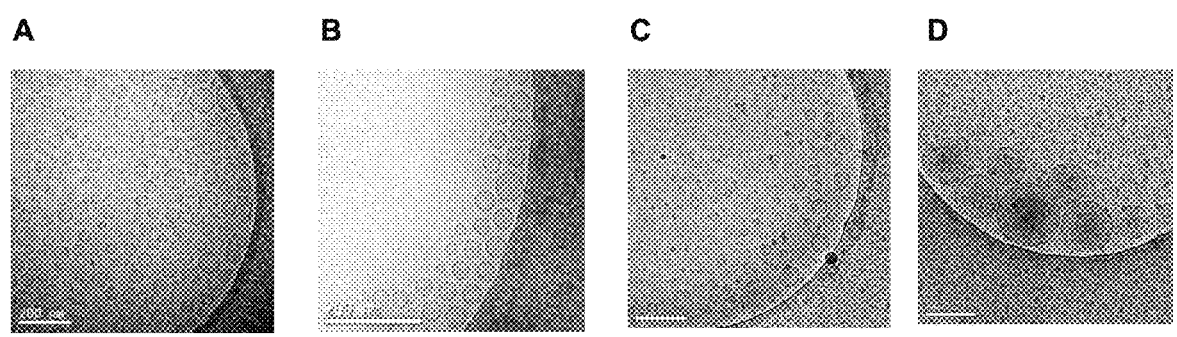
FIG. 3. Pictures of cryo-transmission electron microscopy (Cryo-TEM) of EGF vesicles with cholesterol:CTAB:EGF composition (A), cholesterol:cetrimide:EGF (B), cholesterol:benzalkonium chloride (BKC):EGF composition (C) and β-Sitosterol:CTAB:EGF (D) with QUATs:cholesterol or β-Sitosterol ratio of 1 M:1 M and EGF:cholesterol ratio of 0.684 mM:1 M for (A) and (B), or 0.638 mM:1M for (C). The EGF:β-Sitosterol ratio was 0.717 mM:1 M in (D).

CTAB:cholesterol (1:1) vesicles, with EGF incorporated at a concentration between 1 μM and 40 μM, were obtained. The results for physical appearance, mean size and Z-potential are shown in Table 2; the particle size distribution, in FIG. 2A and the size and morphology, by cryo-TEM, in FIG. 3A. As it can be seen in Table 2, the different preparations, with varying proportions of EGF:cholesterol, were stable. The Z-potentials of all the preparations were positive, and far above +30 mV, which predicts elevated long-term stability. An increase in the mean size and PDI with an increase in the proportion of EGF:cholesterol can also be noticed. In FIG. 2A, very highly homogenous particle size distributions are observed, having an average diameter not exceeding the 200 nm. FIG. 3A shows that, in relation to vesicle morphology studied by cryo-TEM, spheroidal shapes with unilamellar structure predominate. The mentioned characteristics of the different vesicle preparations make them very attractive from the pharmaceutical viewpoint.

TABLE 2

Physical appearance, mean particle size and Z-potential of the different variants of cholesterol:CTAB:EGF vesicles for different compositions

| Composition (EGF:cholesterol) | Physical appearance | Mean size (nm) (PDI)* | Z-Potencial (mV) (±SD)* |
|---|---|---|---|
| 0 mM:1 M | Disperse opalescent solution | 117.7 (0.244) | +73.1 (±11.0) |
| 0.137 mM:1 M | Disperse opalescent solution | 113.6 (0.299) | +75.3 (±10.6) |
| 0.274 mM:1 M | Disperse opalescent solution | 113.7 (0.274) | +72.1 (±5.2) |
| 0.684 mM:1 M | Disperse opalescent solution | 96.6 (0.257) | +70.9 (±9.6) |
| 2.052 mM:1 M | Disperse opalescent solution | 128.4 (0.379) | +74.2 (±10.3) |
| 3.420 mM:1 M | Disperse opalescent solution | 145.4 (0.391) | +74.8 (±6.3) |
| 5.472 mM:1 M | Disperse opalescent solution | 180.6 (0.450) | +68.40 (±5.8) |

*Nano-ZS (Malvern Instruments, United Kingdom),
PDI—polydispersity index

Example 3. Synthesis of Cholesterol:Cetrimide:EGF Vesicles Using Compressed Fluid Technology These vesicles were synthesized in a similar way to those in Example 2, but in this case, an aqueous solution of cetrimide with a concentration of 2.61 mg/mL was used. Cetrimide:cholesterol (1:1) vesicles were obtained, with EGF incorporated at a concentration between 1 μM and 40 μM. The results of physical appearance, mean size and Z-potential are shown in Table 3; the particle size distribution, can be observed in FIG. 2B, and the size and morphology, by cryo-TEM, are shown in FIG. 3B. As it can be seen in Table 3, all the preparations were stable with small mean size and PDI values. The mean size, particle size distribution and the Z-potential were determined by DLS. The Z-potential of all the preparations is positive, and well above +30 mV, which predicts high long-term stability. FIG. 2B shows that the distributions of particle sizes are highly uniform, and their average diameter does not exceed 200 nm. FIG. 3B shows that spheroidal shapes with unilamellar structure predominate, according to cryo-TEM. The different vesicle preparations also have characteristics which make them very attractive from the pharmaceutical viewpoint.

TABLE 3

Physical appearance, mean particle size and Z-potential of different variants of cholesterol:cetrimide:EGF vesicles for different compositions

| Composition (EGF:cholesterol) | Physical appearance | Mean size (nm) (PDI)* | Z-Potencial (mV) (±SD)* |
|---|---|---|---|
| 0 mM:1 M | Disperse opalescent solution | 118.6 (0.392) | +78.1 (±16.1) |
| 0.137 mM:1 M | Disperse opalescent solution | 123.8 (0.381) | +75.4 (±12.6) |
| 0.274 mM:1 M | Disperse opalescent solution | 127.3 (0.376) | +77.3 (±9.3) |
| 0.684 mM:1 M | Disperse opalescent solution | 140.8 (0.375) | +79.1 (±13.1) |
| 2.052 mM:1 M | Disperse opalescent solution | 124.0 (0.388) | +71.1 (±11.6) |
| 3.420 mM:1 M | Disperse opalescent solution | 125.1 (0.436) | +70.4 (±10.8) |
| 5.47 mM:1 M | Disperse opalescent solution | 152.1 (0.44) | +72.7 (±11.2) |

*Nano-ZS (Malvern Instruments, United Kingdom),
PDI—polydispersity index

Example 4. Synthesis of Cholesterol:BKC:EGF Vesicles Using Compressed Fluid Technology These vesicles were synthesized in a similar way to those in Example 2, but in this example, on one hand, it was used a solution of 81.46 mg of cholesterol in 2.88 mL of ethanol, and on the other one, an aqueous solution of 3.0 mg/mL of BKC and EGF at the desired concentration was used. BKC:cholesterol (1:1) vesicles were obtained, with EGF incorporated at a concentration of 5 µM. The results for physical appearance, mean size and Z-potential are shown in Table 4. It can be observed that the vesicle preparation is stable and it has a relatively small mean size and PDI. The mean size, particle size distribution and the Z-potential were determined by DLS. Furthermore, similar to the above mentioned vesicle preparations, that comprise in their composition a cationic surfactant of quaternary ammonium type, they have positive Z-potential values much higher than +30 mV, which predicts high long-term stability for them. FIG. 3C shows that spheroidal shapes with unilamellar structure predominate, according to the vesicle morphology study performed by cryo-TEM. These vesicles also have features that make them very attractive from a pharmaceutical point of view.

TABLE 4

Physical appearance, mean particle size and Z-potential of the cholesterol:BKC:EGF vesicles at the working composition.

| Composition (EGF:cholesterol) | Physical appearance | Mean size (nm) (PDI)* | Z-Potencial (mV) (±SD)* |
|---|---|---|---|
| 0.638 mM:1 M | Disperse opalescent solution | 199.9 (0.335) | +74.4 (±10.0) |

*Nano-ZS (Malvern Instruments, United Kingdom),
PDI—polydispersity index

Example 5. Synthesis of Cholesterol:CTAB:BSA Vesicles Using Compressed Fluid Technology These vesicles were synthesized in a similar way to those in Example 2, but in this case the protein BSA was used in an aqueous solution. CTAB:cholesterol (1:1) vesicles were obtained, with BSA incorporated at a concentration of 0.37 µM, corresponding to 25 µg/mL. The results for physical appearance, mean size and Z-potential are shown in Table 5. It can be seen that the vesicle preparation is stable and they have relatively small mean size and PDI. The mean size, particle size distribution and the Z-potential were determined by DLS. They also exhibit positive Z-potential values, well above +30 mV, which predicts high long-term stability.

TABLE 5

Physical appearance, mean particle size and Z-potential of cholesterol:CTAB:BSA vesicles at the working composition

| Composition (BSA:cholesterol) | Physical appearance | Mean size (nm) (PDI)* | Z-Potencial (mV) (±SD)* |
|---|---|---|---|
| 0 mM:1 M | Disperse opalescent solution | 124.2 (0.283) | +70.1 (±11.0) |
| 0.051 mM:1 M | Disperse opalescent solution | 119.9 (0.378) | +76.5 (±10.6) |

*Nano-ZS (Malvern Instruments, United Kingdom),
PDI—polydispersity index

Example 6. Determination of the Efficiency of Protein Incorporation in the Vesicles To determine the efficiency of EGF incorporation in the vesicles, the ultracentrifugation method was used for separating free EGF vesicles. From the different vesicle suspensions evaluated, 1.0 mL was taken; placed in vials and centrifuged at high speed (100,000×g) for 60 min at 4° C. Subsequently, the protein content in the supernatant (free EGF) was determined by a solid-phase immunoenzymatic assay (ELISA) (Vazquez et al., *Biotecnol. Apl.* 1990, 7: 42-49). The efficiency of EGF incorporation in the vesicles was determined by the following expression:

$$\text{Efficiency of incorporation}(\%) = \frac{[EGF \text{ initial mass} - EGF \text{ mass in the supernatant}] * 100}{EGF \text{ initial mass}}$$

The results are shown in Table 6. Results of the efficiency of EGF incorporation in vesicles with the DPPC:cholesterol composition (obtained in Example 1), the CTAB:cholesterol composition (obtained in Example 2) and the cetrimide:cholesterol composition (obtained in Example 3) are shown. The effect of the EGF concentration (EGF:cholesterol ratio) were also evaluated. Values of high EGF-incorporation efficiency (near 100%) can be observed in QUATs:cholesterol systems, for a wide range of EGF concentrations (EGF:cholesterol ratio). However, the results of the efficiency of EGF incorporation into the DPPC:cholesterol system were very low, since the maximum efficiency of incorporation did not exceed 10%, for the highest EGF concentration.

TABLE 6

Efficiency of EGF incorporation into vesicles of different compositions

| Composition (EGF:cholesterol) | Efficiency of incorporation (%) (Mean ± STDEV, n = 2) | | |
|---|---|---|---|
| | DPPC-cholesterol | CTAB-cholesterol | cetrimide-cholesterol |
| 0.137 mM:1 M | ND | 99.8 ± 1.3 | 99.9 ± 0.5 |
| 0.274 mM:1 M | ND | 99.7 ± 0.9 | 99.3 ± 0.7 |
| 0.684 mM:1 M | ND | 99.7 ± 0.7 | 99.0 ± 0.3 |
| 2.052 mM:1 M | 1.0 ± 0.2 | 99.9 ± 0.5 | 98.5 ± 2.6 |
| 3.420 mM:1 M | 2.7 ± 0.3 | 99.7 ± 0.2 | 98.0 ± 0.5 |
| 5.472 mM:1 M | 8.7 ± 0.6 | 99.9 ± 0.4 | 97.9 ± 1.8 |

ND—Not determined

In the particular case of the vesicles comprising BSA, the same procedure described for EGF was followed, except that the quantification of the protein was performed by the bicinchoninic acid method (Micro-BCA) (Smith et al., Anal. Biochem. 1985, 150: 76-85).

The efficiency of BSA incorporation in the CTAB:cholesterol vesicles, prepared as described in Example 5, was only 42±5%. When the efficiency of BSA incorporation was compared with the EGF incorporation (shown in Table 6), in vesicles with the same CTAB:cholesterol composition, it can be observed that EGF incorporation was significantly higher.

Example 7. Reproducibility of the Synthesis of Cholesterol:CTAB:EGF Vesicles by Compressed Fluid Technology Aiming to test the robustness and reproducibility of the methodology used for the synthesis of EGF vesicles, the mean particle size, PDI, Z-potential and efficiency of EGF incorporation were determined in several batches of 0.684 mM:1 M and 2.052 mM:1 M composition of EGF:cholesterol, prepared on different dates. In Tables 7 and 8, the results obtained are shown. The mean particle size, PDI and Z-potential were determined by DLS. The efficiency of EGF incorporation was determined as described in Example 6.

TABLE 7

Features of CTAB:cholesterol (1:1) vesicles with EGF incorporated at a concentration of 5 µM, after preparation by DELOS-SUSP

| Code (Date) | Particle diameter (nm)* | PDI | Z-Potential (mV)* | EGF incorporation (%) |
|---|---|---|---|---|
| Batch 1 (26 Oct. 2010) | 103.3 | 0.363 | 69.5 | 98.1 |
| Batch 2 (29 Oct. 2010) | 96.75 | 0.376 | 79.7 | 97.3 |
| Batch 4 (10 Feb. 2011) | 101.4 | 0.311 | 77 | 97.2 |
| Batch 8 (18 Nov. 2011) | 92.82 | 0.351 | 76 | 96.6 |
| Batch 10 (10 Feb. 2012) | 113.6 | 0.281 | 75.9 | 95.8 |
| Batch 11 (10 Feb. 2012) | 111.3 | 0.335 | 70.1 | 98.6 |

*Nano-ZS (Malvern Instruments, United Kingdom),
PDI—polydispersity index

TABLE 8

Characteristics of CTAB:cholesterol (1:1) vesicles with EGF incorporated at a concentration of 15 µM after preparation by DELOS-SUSP

| Code (Date) | Particle diameter (nm)* | PDI | Z-Potencial (mV)* | EGF incorporation (%) |
|---|---|---|---|---|
| Batch 3 (29 Oct. 2010) | 141.7 | 0.419 | 80.4 | 99.4 |
| Batch 5 (24 Feb. 2011) | 139.5 | 0.278 | 74 | 98.1 |
| Batch 6 (28 Feb. 2011) | 142.2 | 0.275 | 72.9 | 99.7 |
| Batch 7 (29 Jun. 2011) | 139 | 0.353 | 77 | 99.1 |
| Batch 9 (30 Jun. 2011) | 140.9 | 0.357 | 77.5 | 98.6 |
| Batch 8 12 Jul. 2011 | 141.4 | 0.319 | 76.0 | 99.5 |

*Nano-ZS (Malvern Instruments, United Kingdom),
PDI—polydispersity index

From the values reported in Tables 7 and 8, it can be concluded that the vesicles have similar characteristics, independently of the date of preparation, which allows to state that the DELOS-SUSP method is reproducible and robust for preparation of the EGF vesicles.

Example 8. Scale Up of the Synthesis of Cholesterol:CTAB:EGF Vesicles Using Compressed Fluid Technology The vesicles were synthesized as in Example 2, but on a 50 times greater scale. First, a solution of 3.8 g of cholesterol in 144 mL of ethanol is introduced in the high pressure reactor of 300 mL volume at atmospheric pressure and working temperature (Tw=35° C.). Compressed $CO_2$ is added producing volumetric expansion of the solution to reach a molar fraction $X_{CO2}$=0.7 and a working pressure Pw=10 MPa. To achieve full homogenization and thermal balance, the system is left for about 60 minutes at 10 MPa and 35° C. Finally, the expanded liquid solution is depressurized from the working pressure to atmospheric pressure, on 1200 mL of a solution of CTAB in mQ water (C=2.83 mg/mL) containing EGF at the desired concentration (5 and 12 µM). In this last step, a stream of $N_2$ at 10 MPa is used as a plunger to push the cholesterol in ethanol solution to maintain constant the working pressure inside the reactor during depressurization. Then the vesicles are transferred to a hermetically sealed container and stored until use at 5±3° C.

CTAB:cholesterol (1:1) vesicles with EGF incorporated at a concentration of 5 µM and 12 µM were obtained. The results of physical appearance, mean size, PDI and Z-potential are shown in Table 9. The mean particle size, PDI and Z-potential were determined by DLS.

TABLE 9

Physical appearance, mean particle size, PDI and Z-potential of the variants of cholesterol:CTAB:EGF vesicles, for different compositions, after preparation by DELOS-SUSP, at a pilot scale

| Composition (EGF:choles-terol) | Physical appearance | Mean size (nm) (PDI)* | Z-Potencial (mV) (±SD)* |
|---|---|---|---|
| 0 mM:1 M | Disperse opalescent solution | 132.7 (0.224) | +63.1 (±2.0) |
| 0.684 mM:1 M | Disperse opalescent solution | 127 (0.211) | +61.3 (±2.2) |
| 1.642 mM:1 M | Disperse opalescent solution | 160.7 (0.234) | +60.1 (±2.6) |

*Nano-ZS (Malvern Instruments, United Kingdom),
PDI—polydispersity index

Table 9 shows that EGF:CTAB:cholesterol vesicles are stable at proportions of 0.684 mM:1 M and 1.64 mM:1 M. It can be seen that in the scale up process the particles obtained have physico-chemical characteristics comparable to those obtained in the 6 mL scale (Example 2). In both cases, the mean sizes of the particles obtained are under 200 nm.

Example 9. Biological Activity of the Vesicles, Evaluated by the Cell Proliferation Assay in Murine A31 3T3 Fibroblasts The biological activity of the EGF vesicles, prepared as described in Examples 1 to 3, was determined using a cell proliferation assay (Mire-Sluis and Page, *J. Immunol. Methods* 1995, 187: 191-199). In this case, the ability of free EGF, EGF liposomes and the different vesicles comprising EGF to increase cell proliferation of the A31 3T3 line of murine fibroblasts was evaluated. The biological activity of the different vesicular suspensions was evaluated by applying an appropriate dilution of the suspension directly onto the test cells, in the way that the absorbance of the samples fell within the range of the curve of the working reference material, which was previously calibrated against the international reference material EGF 91/550, provided by the National Institute for Biological Standards and Control (NIBSC, United Kingdom).

With the objective of comparing the potency of the various EGF vesicle preparations with free EGF, the specific activity of the different preparations was calculated from the biological activity results, by the following expression:

$$EGF \text{ specific activity } (IU/mg) = \frac{EGF \text{ biological activity } (IU/mL)}{EGF \text{ concentration } (mg/mL)}$$

The biological activity is measured by the assay described and the protein concentration is given by the nominal value (in mg/mL) of the equivalent EGF concentration in the different vesicle preparations.

As a control in the cell proliferation assay, blank vesicles (without the addition of EGF) were used, in correspondence with the different variants tested. In these samples, at dilutions lower than those used for the vesicles with EGF, neither a cytotoxic effect nor an increase in the proliferation was detected.

Figure 4A:
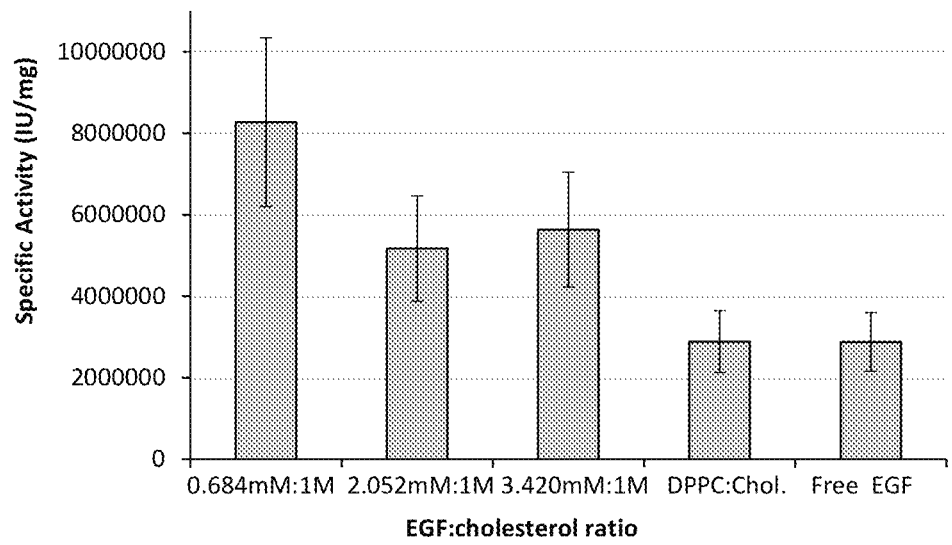
FIG. 4. Specific biological activity of different EGF preparations in a cell proliferation assay, where free EGF, DPPC:cholesterol liposomes (with ratio DPPC:cholesterol 1 M:1 M and EGF:cholesterol 20.3 mM:1 M) and the CTAB:cholesterol vesicles (A) and cetrimide:cholesterol vesicles (B), keeping the QUATs:cholesterol 1 M:1 M ratio constant and varying the EGF:cholesterol (0.684 mM:1 M, 2.052 mM:1 M:1 M and 3.420 mM:1 M) ratio are compared.
Figure 4B:
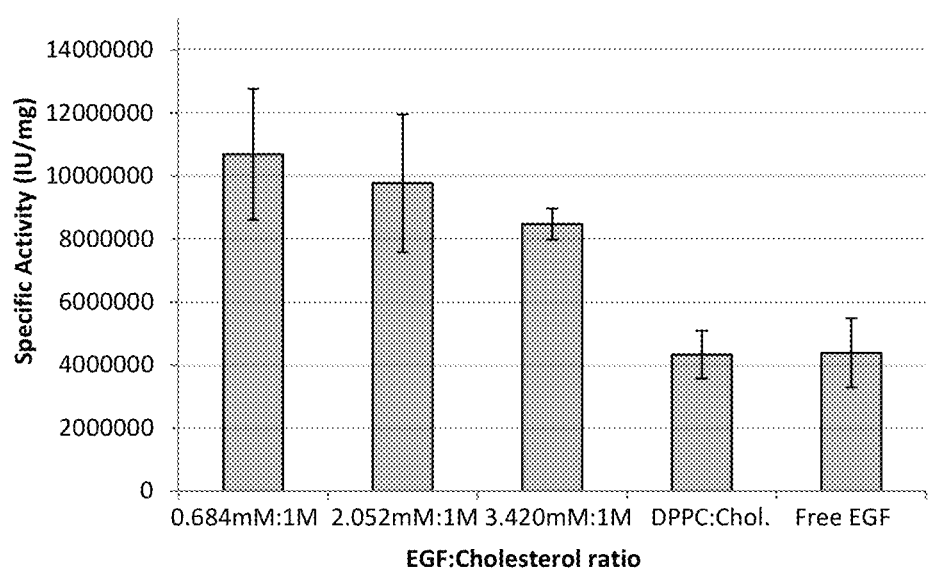

FIG. 4A shows that EGF vesicles with CTAB:cholesterol composition exhibit increased specific activity as compared to free EGF and EGF in vesicles with the DPPC:cholesterol composition. In FIG. 4B, a result similar to the former is also observed when cetrimide, instead of CTAB, was used in the composition of the vesicles prepared by the same procedure. The purpose of this evaluation was to determine if the EGF biological function is affected by the components or by the synthesis process of said vesicles. However, for the vesicles with QUATs:cholesterol composition, an unexpected increase in the specific biological activity of EGF was found.

Example 10. Protease Resistance of EGF Integrated into QUATs:Cholesterol Vesicles EGF vesicles with QUATs:colesterol (1:1) compositions, prepared as in Examples 2 and 3 of the present invention, were used. This experiment was performed to evaluate the ability of QUATs:cholesterol vesicles to preserve the stability of integrated EGF against proteases. It is known that chronic wounds, such as diabetic foot ulcers, have proteolytic environments that may affect the bioavailability of the drugs used to treat them (Bennett and Schultz, *Am. J. Surg.* 1993, 166: 74-81).

For this evaluation, trypsin was used as a model protease. The enzymatic reaction was prepared in Tris-HCl buffer with pH 8.5 and 20 mM concentration, containing a final concentration of 0.5 µg/mL of trypsin. The final concentration of free EGF or the EGF equivalent in the different vesicle preparations was 125 µg/mL. Incubation of the samples was performed for periods of 4, 8, 16 or 24 hours at 37° C. Trifluoroacetic acid (TFA), at a final concentration of 0.1% (v/v) was used to stop the enzymatic reaction.

After stopping the reaction, samples were diluted in absolute methanol, to a final methanol concentration of 80% (v/v), stirred and centrifuged in a table centrifuge at 10 000 rpm for 5 minutes. Finally, the centrifugation supernatants were filtered through polycarbonate filters of 0.2 µm pore size and then applied to a HPLC system (Merck, Germany). The EGF standard and vesicle samples were analyzed using a $C_{18}$ reverse phase column (Vydac, Hesperia, Calif., USA) and detected at 226 nm. To do this, a linear gradient of 20% to 40% of B for 28 minutes was used. Mobile phase A consists of 0.1% TFA/water and mobile phase B consists of 0.05% TFA/Acetonitrile. The injection volume analyzed was 5.0 mL, corresponding to about 20 µg of EGF. The flow rate used was 1.0 mL/minute. The EGF concentration in the samples was quantified by interpolation using a calibration curve of the EGF in the area under the main peak and the EGF concentrations of known samples, from the chromatograms obtained at 226 nm. The percentage of EGF remaining in each sample, after incubation with trypsin, was calculated using the following expression:

$$\text{Remaining } EGF \text{ } (\%) = \frac{EGF \text{ conc. after trypsin incubation } (\mu g/mL) * 100}{EGF \text{ conc. before trypsin incubation } (\mu g/mL)}$$

Figure 5A:
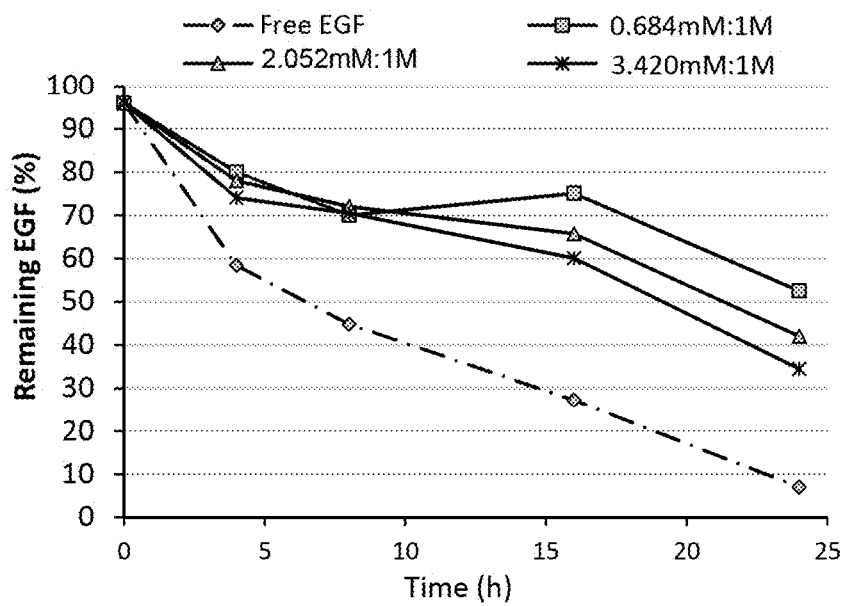
FIG. 5. Proteolytic degradation profile, after exposure to trypsin at 37° C. during different time intervals, of free EGF and different vesicle preparations keeping constant the CTAB:cholesterol ratio (A) and the cetrimide:cholesterol ratio (B) at 1 M:1 M and varying the EGF:cholesterol ratio (0.684 mM:1 M, 2.052 mM:1 M and 3.420 mM:1 M).
Figure 5B:
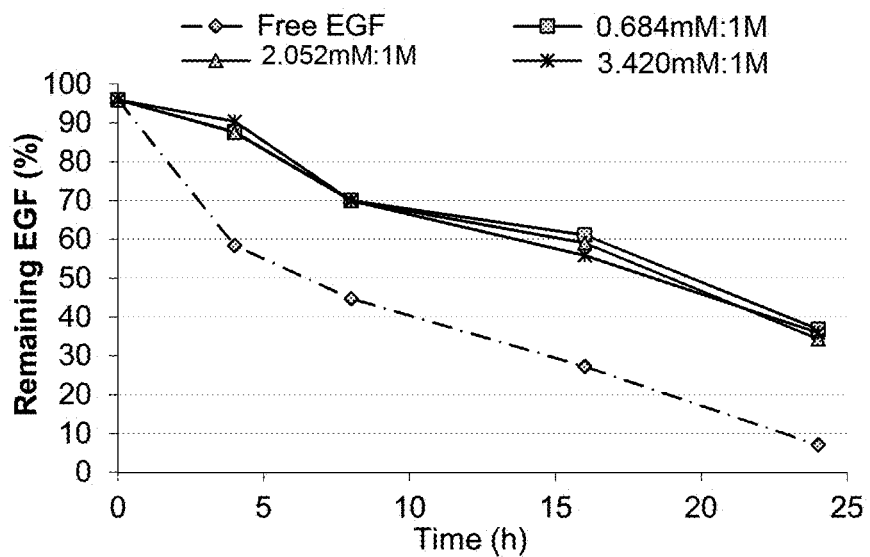

FIG. 5A shows that EGF vesicles with CTAB:cholesterol composition exhibit increased stability against trypsin, compared to free EGF, during a period of 24 hours. Similarly, FIG. 5B, shows that EGF vesicles with cetrimide:cholesterol composition show a similar behavior to the one described before. Significant differences were not found among the different EGF loads evaluated (EGF:cholesterol ratio).

The results of the stability to proteases, of EGF incorporated in QUATs:cholesterol vesicles, showed that EGF vesicles have much higher stability than free EGF.

Example 11. Demonstration of the Antimicrobial Activity of QUATs:Cholesterol Vesicles Vesicle suspensions comprising QUATs:cholesterol were evaluated to determine if they showed antimicrobial activity. This activity was determined using the agar diffusion method (*Manual of Clinical Microbiology. 6th ed. Washington, DC: ASM;* 1995). The effectiveness of the different suspensions was assayed against Gram positive bacteria (*Bacillus subtilis, Staphylococcus aureus*), Gram negative bacteria (*E. coli, Proteus mirabilis*), and against fungi (*Candida albicans, Aspergillus niger*) using the technique of wells in nutrient agar plates. These microorganisms were identified and provided by the microorganism collection BCCM/LMG (Belgium). Bacteria were grown overnight at 37° C. in Tryptone Soy Broth (Oxoid), and fungi were incubated for 72 hours at 28° C. in Sabouraud Dextrose Broth (Oxoid). These suspensions were used as inocula. A final inoculum, using 100 µl of a suspension containing $10^8$ colony forming units/ml of bacteria, or $10^4$ spores/ml of fungus, was spread on Tryptone Soy Agar and Sabouraud Dextrose Agar (Oxoid) plates, respectively. The disk (6 mm in diameter) was impregnated with each of the different vesicle suspensions to be tested. Ciprofloxacin and fluconazole (100 µg/ml) were used as positive controls for bacteria and fungi, respectively. Assay plates were incubated at 37° C. for 24 hours for bacteria, and 28° C. during 72 hours for fungi, depending on the incubation time required for visible growth.

Table 10 shows that the different vesicle suspensions had antimicrobial effect against Gram positive bacteria and fungi. In general, microorganisms were more sensitive to vesicular suspensions of cetrimide:cholesterol composition than those of CTAB:cholesterol. Some vesicular suspensions showed antibacterial and antifungal activity against certain microorganisms comparable to ciprofloxacin and fluconazole, respectively.

TABLE 10

Antimicrobial and antifungal activity of different vesicle suspensions of QUATs:cholesterol against bacteria and fungi.

| Vesicular suspensions | Antimicrobial activity (Inhibition zone, mm) | | | | Fungicidal activity (Inhibition zone, mm) | |
|---|---|---|---|---|---|---|
| | *B. subtilis* | *S. aureus* | *E. coli* | *P. mirabilis* | *A. niger* | *C. albicans* |
| CTAB:cholesterol (1:1) | 22 | 18 | R | 10 | 16 | 16 |
| CTAB:cholesterol (1:1) with EGF incorporated at 5 µM | 12 | 6 | R | 4 | 6 | 6 |
| Cetrimide:cholesterol (1:1) | 26 | 16 | 4 | 14 | 18 | 18 |
| Cetrimide:cholesterol (1:1) with EGF incorporated at 5 µM | 24 | 18 | 4 | 10 | 18 | 18 |
| Control | — | — | — | — | — | — |
| Ciprofloxacin | 22 | 20 | 18 | 18 | — | — |
| Fluconazole | — | — | — | — | 21 | 22 |

R—Resistant

Example 12. Manufacture of a Liquid Spray Atomizer Formulation Containing EGF Vesicles A vesicle suspension of CTAB:cholesterol (1:1) with EGF:cholesterol composition of 0.684 mM: 1 M, obtained as in Example 2, with EGF equivalent concentration of 25 µg/mL, was diluted to the EGF equivalent concentration of 15 µg/mL in 10 mM sodium phosphate buffer pH 7.2. This final solution also contains 17% (v/v) glycerol, 10% (v/v) ethanol, 0.02% (w/v) butyl hydroxytoluene (BHT), 0.18% (w/v) of methyl paraben and 0.02% (w/v) of propyl paraben. The resulting dispersion was filtered through 0.2 µm cellulose acetate sterilizing filters, and dispensed in glass vials under nitrogen atmosphere.

Example 13. Manufacture of a Gel Formulation Containing EGF Vesicles

A vesicle suspension of cetrimide:cholesterol (1:1) with EGF:cholesterol composition 0.684 mM M: 1 M, obtained as in Example 3, with EGF equivalent concentration 25 µg/mL, was diluted to the equivalent concentration of 15 µg/mL This formulation contains 10 mM Tris-HCl buffer pH 7.2, and Carbomer (Carbopol 940), to a final concentration of 1.25% (w/v); glycerol, 3% (w/v) and 20 mM of L-methionine. Furthermore, the formulation contains 0.02% (w/v) BHT, and as antimicrobial preservative 0.18% (w/v) methyl paraben and 0.02% (w/v) propyl paraben.

Example 14. Manufacture of a Parenteral Formulation Containing EGF Vesicles

A vesicle suspension of BKC:cholesterol (1:1), with EGF:cholesterol 0.638 mM:1 M composition, obtained as in Example 4, with EGF equivalent concentration of 25 µg/mL, was introduced in the cell of the tangential flow ultrafiltration device Sartocon Slice 200. For ultrafiltration of the vesicles, cassettes with Hydrosart® membranes of 30 kDa pore size were used. The concentration-diafiltration process is conducted at a temperature of 25±3° C. and the maximum pressure drop at the entrance of the cassette was maintained lower than 4 bar. During the process, the suspension was concentrated 5 times (final equivalent concentration of EGF of 125 µg/mL). After the concentration step, the vesicles were diluted in 10 mM sodium phosphate buffer pH 7.2, to an equivalent concentration of 75 µg/mL of EGF. This formulation also contains 20 mM of L-methionine and 0.02% (w/v) of BHT. The resulting suspension was filtered through a 0.2 µm sterilizing filter and dispensed in glass vials under nitrogen atmosphere.

Example 15. Comparison of the Pharmacodynamic Effect of Liposomes and Vesicles Comprising EGF in Animal Models of Wound Healing Experimental Methodology To evaluate the pharmacological efficacy of the formulations listed below, an experimental model of chronic ulcer of total thickness was developed on the back of rats. Sprague Dawley rats of 250-270 grams weight, which were randomly assigned to form 7 experimental groups, of 10 animals each, were used. Rats were intraperitoneally anesthetized with a combination of ketamine/xylazine to extensively depilate their dorsal region. Two symmetrical bilateral retroscapular ulcers were made of 8 mm diameter and total thickness up to the upper fascia, which was spared. Immediate application of triamcinolone acetonide, as compresses, was begun, once a day during the first three days, to stop healing and induce the characteristic changes of chronicity. After 7 days, the interruption of the healing process and chronicity of the ulcers were corroborated by the absence of granulation tissue and hypertrophy of the epithelial edges. From this moment, application of the studied treatments started as described below:

Group 1: treatment-free (saline). They were subjected to the same conditions of handling and manipulation of the rest of the groups. Sterile physiological saline solution was applied in nebulized form.

Group 2: empty DPPC-cholesterol liposomes,

Group 3: empty CTAB-cholesterol vesicles,

Group 4: empty cetrimide cholesterol vesicles,

Group 5: DPPC-cholesterol liposomes loaded with EGF at a concentration of 25 µg/ml, Group 6. CTAB-cholesterol vesicles loaded with EGF at 25 µg/ml, Group 7. Cetrimide-cholesterol vesicles loaded with EGF at 25 µg/ml.

Wounds were cleaned daily. After sanitizing them, each group was administered the suspension indicated in each case. The application of the suspensions was performed twice daily, for 14 days. The experimental systems were treated by topical application of the suspensions of vesicles, or liposomes, by nebulization. All animals were subjected to autopsy and sampling 14 days after the onset of the treatment assigned to each group. Samples were fixed in 10% neutral formalin, and 72 hours later were hemisected uniformly, for later inclusion in paraffin. The stains used were: hematoxylin-eosin, Mallory's trichrome reaction, Verhoeff's and Gomori's reticulum method. The samples were blindly analyzed by two independent researchers.

Results:

It was not necessary to exclude contaminated ulcers; thus, 20 lesions were used for each of the 6 experimental groups. Briefly, it was corroborated that all pharmaceutical presentations of the EGF vesicles significantly stimulated the overall healing process, when compared to groups with EGF-free vesicles (blank), liposomes loaded with EGF at 25 µg/ml, and the experimental control group treated with saline. The data reported relate to the average of two independent studies made at different times. Mann-Whitney U and Student's t-test were used to make the comparisons. All the parameters met the criteria of normal distribution. The parameters studied and the results are shown in Table 11.

TABLE 11

Pharmacodynamic effect of the suspensions evaluated in a chronic wound model in rats

| Experimental group | Inflammatory infiltrate (grades 1-5) | Fibroangiogenic response (1-5 points) | Epithelial migration (en microns) | % of contraction of the edges |
|---|---|---|---|---|
| Group 1: saline | 4.61 ± 1.03 | 2.87 ± 0.65 | $3.0 \pm 1.1 \times 10^3$ | 23.6 ± 5.11 |
| Group 2: empty DPPC-cholesterol liposomes | 4.27 ± 0.02 | 3.2 ± 0.96 | $2.5 \pm 0.7 \times 10^3$ | 18.55 ± 3.21 |
| Group 3: empty CTAB-cholesterol vesicles | 3.8 ± 1.00 | 2.56 ± 0.93 | $2.97 \pm 1.6 \times 10^3$ | 21.9 ± 4.63 |
| Group 4: empty cetrimide-cholesterol vesicles | 4.51 ± 0.95 | 2.64 ± 0.55 | $2.8 \pm 1.5 \times 10^3$ | 31.02 ± 1.81 |
| Group 5: DPPC-cholesterol liposomes loaded with EGF | 2.9 ± 0.88* | 3.81 ± 0.87* | $4.6 \pm 1.04 \times 10^{3}$* | 63.7 ± 6.75* |
| Group 6: CTAB-cholesterol vesicles loaded with EGF | 1.18 ± 0.04** | 4.2 ± 0.18** | $6.27 \pm 0.27 \times 10^{3}$** | 88.7 ± 6.26** |
| Group 7: cetrimide-cholesterol vesicles loaded with EGF | 1.12 ± 0.07** | 4.17 ± 0.25** | $7.02 \pm 0.53 \times 10^{3}$** | 85.3 ± 7.01** |

*Denotes a value of $p \leq 0.05$;
**Denotes a value of $p \leq 0.01$.

The experiment shows that CTAB-cholesterol and cetrimide-cholesterol vesicles loaded with EGF had a potent healing effect. The anti-inflammatory effect observed for groups 6 and 7 is notable compared with the other treatments. It is possible that the effect of promoting fibroangiogenesis and contraction is connected to the reduction of balance of immuno-inflammatory cells infiltrating the neodermis. Similarly, a marked effect promoting epithelial migration was evidenced, microscopically demonstrating the presence of a stratified epidermis. The response obtained for the group treated with EGF-loaded liposomes was less than the one detected in groups 6 and 7. Superiority of the treatments including suspensions of vesicles loaded with EGF, applied to groups 6 and 7, was also revealed in a similar experiment where chronicity in the wounds was induced by topical application of methylglyoxal.

Example 16. Treatments Based on the Topical Application of Vesicles Comprising EGF in Patients with Diabetic Foot Ulcers In clinical cases, most of the treated lesions exceeded 90% probability of requiring amputation, according to the University of Texas scale. Treatments were administered topically.

General Characteristics of the Treated Patients:

They had diabetes mellitus types I or II of long evolution and were medicated with insulin, sulfonylureas, or biguanides, as oral hypoglycemic agents. They had a personal history of poor scarring, while some of them had experienced prior contralateral amputation. All treated lower limb injuries corresponded to ischemic or neuropathic diabetic foot. Lesions, as a whole, were classified as chronic, complex and recalcitrant. The evolution period of the lesions ranged between less than one month and seven years. The size of the treated lesions ranged between 20 and 80 square centimeters. The depth in some lesions even involved the periosteum. From an anatomical point of view, the treated lesions were in the lateral, calcaneus and/or metatarsal regions. All patients received the first treatments hospitalized, as long as exeresis procedures under anesthesia, as well as parenteral antibiotic therapy were necessary. Upon healing, or total wound granulation with evidence of epithelial migration, the patients were subjected to an outpatient regimen and a follow up on alternate days for cure and medication. After complete epithelialization, each patient was followed up for 12 months after healing. Evaluation of the occurrence of relapses, registry of adverse reactions, and assessment of the patient general status were carried out for this purpose.

Table 12 shows the demographic and epidemiological characteristics of the cohort of patients receiving topical treatments.

TABLE 12

Demographic and epidemiological features of the cohort of patients that received topical treatment

| Identif. | Age | Sex | Type of DM* | Duration of DM evolution | Classification of the lesion | Evolution of the lesion | Type of lesion |
|---|---|---|---|---|---|---|---|
| JLG | 56 y** | M | II | 15 y | Neuropathic with ischemic component | 2 years | Frontal extended, residual after transmetatarsal amputation |
| OFS | 65 y | F | II | 17 y | Neuropathic with proximal calcified pattern | 21 days | Wagner III. Anterolateral part of the foot. Lower right extremity |
| AVL | 52 y | M | II | 9 y | Pure neuropathic | 7 years | Plantar, granulated for 7 years without evidence of contraction/epithelialization |
| PAT | 47 y | M | II | 12 y | Ischemic with Ankle brachial index (ABI) of 0.5 32 | 32 days | Wagner IV. Transmetatarsal amputation residual base |
| GMA | 69 y | M | II | 10 y | Pure neuropathic | 6 months | Frontal, residual after transmetatarsal amputation |

*DM: Diabetes mellitus,
**y: years

Figure 6:
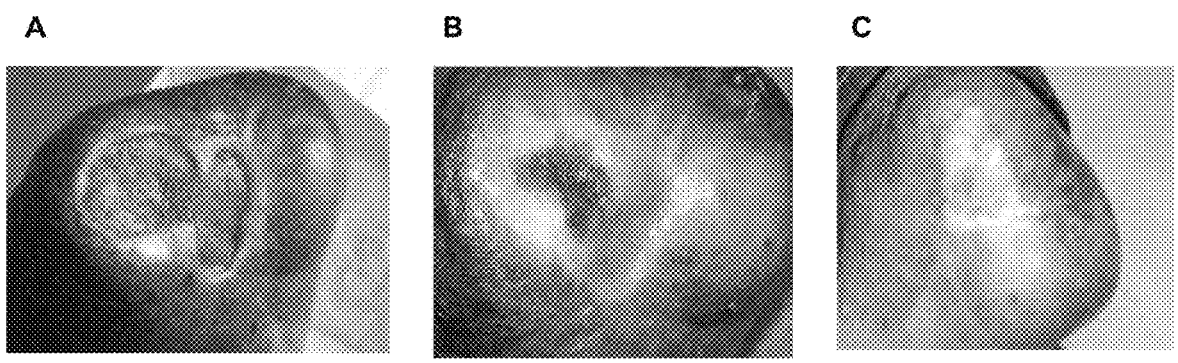
FIG. 6. Photographs of the healing evolution of the diabetic foot ulcer corresponding to patient JLG at treatment onset (A), after 4 weeks (B) and 8 weeks (C) of treatment with a topical spray formulation containing vesicles with CTAB:cholesterol ratio 1 M:1 M and EGF:cholesterol ratio 0.684 mM:1 M, with an EGF equivalent concentration of 15 μg/mL.

The treatment followed with each of the patients is described below:

Patient JLG. Male, 56 years old, controlled with insulin and without any other clinically manifest diabetes complications. Has extensive frontal lesion with ischemic component, which persists two years after transmetatarsal amputation. There were no granulation and epithelialization processes after establishment of antimicrobial and ozone therapies for two years. After performing surgical cleaning and stimulation of the edges, treatment was begun on alternate days using the topical spray formulation described in Example 12 containing EGF:CTAB:cholesterol vesicles. In eight weeks of treatment, complete epithelization of the lesion was achieved. The results are shown in FIG. 6.

Patient OFS. Female, smoker, obese, with history of blood hypertension, controlled with oral hypoglycemic agents. Rapidly advancing necrosis of soft tissue and tendons develops from a local insect bite. Surgical exeresis of the necrotic material is performed. Antimicrobial therapy is started and the lesion is cured on alternate days. Because 14 days after the intervention, the granulation process is torpid and slow, treatment application is begun on alternate days using the topical spray formulation described in Example 12, containing EGF:CTAB:cholesterol vesicles. In eight weeks of treatment, full epithelialization of the lesion was achieved.

Patient AVL. Male, 52 years old, controlled with glibenclamide, Charcot neuropathic plantar foot lesion that has granulated for 7 years, without evidence of contraction/epithelialization. After surgical cleaning and edge stimulation, treatment was started on alternate days using the topical formulation in gel form described in Example 13, containing EGF:cetrimide:cholesterol vesicles. In eight weeks of treatment, complete epithelialization of the lesion was achieved.

Patient PAT. Male, 47 years old, without other co-morbidities or clinically manifest complications of diabetes, even after peripheral arterial disease was detected. As a result of local trauma, a transmetatarsal abscess developed that lead to liquefactive necrosis of nearly all the forefoot with notable phlogistic signs. Transmetatarsal amputation was performed and antibiotic therapy was begun. As a result of the amputation residual base unsatisfactory progress after 30 days, having to carry out extensive debridements due to the presence of ischemic microplaques; intervention was started with the topical formulation in gel form described in Example 13, containing EGF:cetrimide:cholesterol vesicles. The formulation was applied on the edges and wound surface. The treatments were performed on alternate days and extended during 4 weeks. Since the first administration, the presence of ischemic plaques was eliminated and a productive and bleeding granulation tissue began to develop, which later facilitated application of a partial-thickness skin-free graft.

Patient GMA. Male, 69 years old, controlled with insulin and without clinically manifest diabetes complications. The patient has a frontal residual lesion that persists six months after transmetatarsal amputation. There were no granulation and epithelialization processes after 3 months of antimicrobial and ozone therapies. After performing surgical cleaning, treatment was carried out on alternate days with the topical spray formulation described in Example 12, containing EGF:CTAB:cholesterol vesicles. In six weeks of treatment, complete epithelialization of the lesion was achieved.

Example 17. Treatments Based on the Infiltration of EGF Vesicles in Patients with Diabetic Foot Ulcers In clinical cases, most of the treated lesions exceeded 90% probability of requiring amputation according to the University of Texas scale. Treatments were administered by infiltration. The general features of the treated patients correspond with those described in Example 16.

The parenteral formulation referred to in Example 14, which uses EGF:BKC:cholesterol vesicles was used for the infiltrative treatment. The essence of this treatment consists in intra- and perilesional internal injection in the edges and bottom of the lesion, at equidistant points. The material is deposited directing the needle to the base of the ulcer or the depth of the wedge at an angle of 15-45 degrees, always including the dermal-epidermal junction to stimulate contraction of the edges. At each point between 100 and 1000 µL were deposited, depending on the clinical appearance of the tissue and its characteristics. This is performed two to three times per week. The lesions treated and demographic features of the treated population are described in Table 13. In all treated cases, minor or major amputations were prevented.

TABLE 13

Demographic and epidemiological features of the cohort of patients that received infiltrative treatment

| Identif. | Age | Sex | Type of DM* | Duration of DM evolution | Classification of the lesion | Evolution of the lesion | Type of lesion |
|---|---|---|---|---|---|---|---|
| HCJQ | 65 y** | F | II | 13 y | Ischemic, no distal pulses, 0.05 ABI | 33 days | Wagner IV. Amputation of $5^{th}$ toe residual base |
| OFW | 53 y | M | II | 21 y | Neuropathic with calcified macroangiopathy and BI 1.2 | 81 days | Wagner IV. Transmetatarsal amputation residual base |
| JIFM | 61 y | F | II | 16 y | Ischemic with pulse absence and 0.5 ABI | 21 days | Wagner V. Necrotizing fasciitis in plantar and metatarsal areas of the left lower extremity |

*DM: Diabetes mellitus,
**y: years

The treatment followed with each of the patients is described below:

Patient HCJQ. Ischemic, without distal pulse and occluded from the popliteal sector. The lesion is a lateral amputation residual base of the fifth toe, showing exposed capsules and tendon clearly in ischemic necrosis. The lesion was classified as grade IV according to the Wagner scale. Its size was 10×4 centimeters. Treatment is established, when, on the sixth day of amputation, the amputation residual base was found in clinical atony and cyanosis, progressing in this way for five days, despite all systemic and local pharmacological measures. Infiltrations were initiated after surgical debridement of necrotic material, expecting improvement of the local microenvironment and promotion of granulation tissue development. This was first observed after the fifth infiltration session. The patient received a total of 12 sessions of infiltration. The treatment favored the presence of productive and bleeding granulation tissue. Intensive centripetal epithelial migration was observed, although there was no notable contraction of the edges. After 38 days of treatment onset, the lesion was completely epithelialized without requiring a graft. There were no acute or delayed adverse reactions. At 12 months, the lesion was free of local recurrences.

Patient OFW. Neuropathic, 81 days of evolution with trans-metatarsal amputation residual base classifiable as Wagner IV at the time of admission. The size of the lesion is 14×7 square centimeters. Distal pulses are perceived with an ABI of 0.9, despite showing signs of dysesthesia. The treatment is established when, during 42 days of local cures and application of physiological saline compresses, the lesion shows very poor granulation response. Infiltrations begin and are performed daily during the first week of treatment to rescue the local cells. Subsequently, the schedule continues 2 times a week, for three weeks. With this schedule, full productive and bleeding granulation was achieved. The tissue was covered with a partial-thickness skin graft obtained from the contralateral anterior thigh. Similar to the patient previously described, the treatment was well tolerated and a year later the lesion was still epithelialized.

Patient JIFM. Female, former smoker, 61 years old, ABI of 0.4 in the left lower extremity, shows necrotizing fasciitis in the metatarsal and plantar foot areas. The lesion is classified as grade V Wagner scale. The patient was treated surgically; excision of all necrotic tissue and/or contaminated soft tissue and bone was carried out. Systemic polyvalent antibiotic therapy is established. After 48 hours of the surgery, the first inspection of the lesion was made, local cleaning performed, and infiltrative treatment with the vesicles is begun. During the first 10 days, a treatment regimen of attack doses of EGF vesicles was installed, which later could be reduced to two infiltration sessions during 5 weeks. The treatment helped save a foot without any other therapeutic alternative. The patient has normal gait and satisfactory motor command of the distal portion of the limb.

Example 18. Treatments Based on the Combined Application of Infiltrative and Topical EGF Vesicles in Patients with Diabetic Foot Ulcers In clinical cases, most of the treated lesions exceeded 90% probability of requiring amputation, according to the scale established by the University of Texas. Treatments were administered combining the topical and infiltrative routes. The general characteristics of the patients treated correspond with those described in Example 16.

For the combined treatment, infiltration was used first, using the parenteral formulation comprising EGF vesicles (referred to in Example 14). Afterwards, for the topical application, the spray described in Example 12 and the gel described in Example 13 were alternatively used.

The demographic characteristics of the treated population and the lesions are described in Table 14. In all cases treated the minor or major amputations were prevented.

TABLE 14

Demographic and epidemiological characteristics of the cohort of patients that received a combination therapy including infiltration and topical treatment

| Identif. | Age | Sex | Type of DM* | Duration of DM evolution | Classification of the lesion | Evolution of the lesion | Type of lesion |
|---|---|---|---|---|---|---|---|
| AFG | 74 y** | M | II | 22 y | Ischemic, popliteal occlusive pattern, ABI of 0.5 | 20 days | Wagner V Necrosis of the calcaneus soft tissue and bone involvement |
| LATR | 61 y | F | II | 18 y | Ischemic - aortic bifemoral with macroangiopathy, 0.4 ABI | 50 days | Wagner IV Supracondylar amputation residual base with ischemic plaque |
| ZEM | 57 y | F | II | 22 y | Pure neuropathic | 7 years | Plantar extensive, granulated for 7 years with no evidence of contraction/epithelialization |

TABLE 14-continued

Demographic and epidemiological characteristics of the cohort of patients that received a combination therapy including infiltration and topical treatment

| Identif. | Age | Sex | Type of DM* | Duration of DM evolution | Classification of the lesion | Evolution of the lesion | Type of lesion |
|---|---|---|---|---|---|---|---|
| JLHB | 63 y | M | II | 18 y | Neuro-ischemic | 7 years | Wagner IV Soft tissue abscess in the sole and inner-middle lateral region of the right lower extremity |

*DM: Diabetes mellitus,
**y: years

Below, the treatment followed with each of the patients is described.

Patient AFG. Male with a long history of diabetes and history of poor adherence to treatments. The patient shows popliteal occlusion pattern with absence of distal pulses. The lesion debuts as a phlyctena that is contaminated and rapidly advances to necrotize all soft tissues of the calcaneus region. During a first surgical cure soft tissues are removed. Five days later, another surgery is necessary, which leads to devastation of bone material. Intensive polyvalent antibiotic therapy is established and 20 days after the first surgery, infiltrative treatment with EGF vesicles is started. A daily treatment session and local cure is established for the first two weeks. This is followed by cures and treatment on alternate days using the topical gel formulation described in Example 13 containing EGF:cetrimide:cholesterol vesicles prepared according to Example 3, on the edges and wound surface, during the following 8 weeks. After 10 weeks of treatment, the lesion was completely epithelialized.

Patient LATR. Ischemic, lacking distal pulses and with macrovascular disease of both lower limbs. ABI is 0.6, with no possibility of revascularization surgery due to calcifications. Prior contralateral amputation was performed three years ago. Has fine artery thrombosis in the fourth and fifth toes, which were both amputated with extensive deep lateral wedge. Two weeks after surgery, the amputation residual base showed signs of atony and was refractory to granulation. Therefore in the third week, treatment with the vesicles was started, initially by infiltrative treatment with a dose between 25 and 125 µg of EGF per point of injection, deposited in the edges and bottom of the surgical area. This treatment modality is used until all cavities and tunnels are filled with granulation tissue, which took place approximately after three weeks. Subsequently, it was decided to continue the treatment topically, by using gel with the composition described in Example 13, containing EGF:cetrimide:cholesterol vesicles. The treatment is performed on the edges and wound surface, especially focusing on the dermo-epithelial border of the wounds to stimulate re-epithelialization. The treatment was performed on alternate days until complete epithelialization in 5 weeks.

Figure 7:
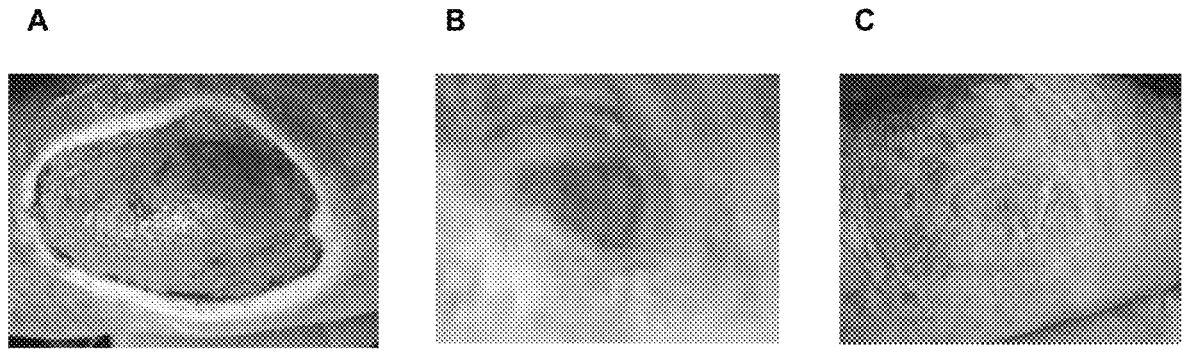
FIG. 7. Photographs of the healing evolution of the diabetic foot ulcer corresponding to patient ZEM at treatment onset (A), after 4 weeks (B) and 8 weeks (C) of treatment. During the first 4 weeks the treatment was carried out by infiltration with a parenteral formulation containing vesicles with BKC:cholesterol ratio 1 M:1 M and EGF:cholesterol ratio 0.638 mM:1 M, with an equivalent concentration of EGF of 75 μg/mL. The other 4 weeks, to complete 8 weeks, the treatment was carried out by using a topical spray formulation containing vesicles with CTAB:cholesterol ratio 1 M:1 M and EGF:cholesterol ratio 0.684 mM:1 M, with an equivalent concentration of EGF of 15 μg/mL.

Patient ZEM. Female, 57 years old, with Wagner grade III lesion and evidence of neuropathy, plantar lesion has granulated for 7 years, but there is no evidence of contraction/epithelialization. After surgical cleaning and stimulation of the edges, infiltrative treatment was carried out with a dose of 75 µg of equivalent EGF per injection point, using the formulation described in Example 14 containing EGF:BKC:cholesterol vesicles, deposited in the edges of the surgical area. This treatment modality was applied during the first four weeks on alternate days. Subsequently, it was decided to continue using the treatment on alternate days with the topical spray formulation described in Example 12 containing EGF:CTAB:cholesterol vesicles. EGF vesicles are atomized on the edges and surface of the lesion; with special focus on the dermo-epithelial border of the wounds to stimulate re-epithelialization, the treatment is performed on alternate days until complete epithelialization in 8 weeks. The evolution of the healing process is shown in FIG. 7.

Patient JLHB. Neuropathic, developed an extensive infectious lesion as consequence of a dry burn on the foot of the right lower extremity. It finally leads to transmetatarsal amputation, to which a 10-centimeter lateral wedge is added. Treatment is started with intravenous antibiotics and systematical local cures every 48 hours. The lesion showed tendency to granulate very slowly and atony of the edges 20 days after surgery. Infiltrative treatment is begun with vesicles loaded with 75 µg of EGF on alternate days in the residual base, as well as the wedge. By the third week of treatment the application starts, on alternate days, with the topical spray formulation described in Example 12 containing EGF:CTAB:cholesterol vesicles, reaching the deep zone of the lateral wedge. The treatment combination accelerated total granulation and spontaneous epithelialization over an area of more than 60 square centimeters.

Example 19. Demonstration of the Therapeutic Efficacy of the Use of EGF Vesicles in a Lethal Model of Acute Lung Injury (ALI) or Adult Respiratory Distress Syndrome (ARDS) in Rats Male Sprague Dawley rats with body weight between 250 and 280 grams were used. Lung injury was induced under general anesthesia (ketamine/xylazine) by intratracheal instillation of a combination of lipopolysaccharide (LPS)-zymosan. Immediately afterwards, the animals were randomly assigned to three experimental groups of 12 animals each.

Group A: treated with physiological saline.
Group B: treated with an spray of EGF in physiological saline at a concentration of 25 µg/ml/kg.
Group C: treated with cholesterol:BKC:EGF vesicles described in Example 4, with equivalent concentration of 25 µg/ml of EGF, and administered as in Group B.

The animals were allowed to evolve without any treatment until the onset of the first symptoms. Six hours after the application of LPS/zymosan, rats showed tachypnea associated with forced exhalation. At this point, the animals showed arterial $PO_2$ saturation of 65% and clear respiratory acidosis.

Therefore, treatments were begun approximately 8 hours after the toxins were instilled. The experiment was aimed at evaluating the effect of treatment with both EGF formulations solely on the acute phase of ARDS. The treatments were performed by orofacial mask adapted from a volatile anesthesia machine. Treatments were performed twice daily. The animals were also treated once a day with hydrocortisone acetate (10 mg/kg) as coadjuvant treatment.

After 72 hours of treatment onset, the study was stopped. Surviving animals were anesthetized and subjected to deep bronchoalveolar lavage in 5 ml of sterile saline for cytological and biochemical study, as well as arterial blood sampling for determination of blood gas parameters. Then the lungs were insufflated with 10 ml of 10% neutral formalin and processed for histology.

Table 15 shows the daily mortality results per group. As it can be seen, the treatment with EGF nebulization controlled the progression of acute lung injury. Notably, the best effect in terms of survival was in the group that received EGF incorporated into vesicles. This suggests that prolonged occupation of multiple EGF receptors exerts a more consistent pharmacological effect than EGF as particles in a simple liquid aerosol in physiological saline.

TABLE 15

Mortality in each group

| Group | 24 hours | 48 hours | 72 hours | Death total |
|---|---|---|---|---|
| A | 3 | 6 | 1 | 10 (83.3%) |
| B | — | 5 | — | 5 (41.6%) |
| C | 2 | — | — | 2 (16.6%) |

The results of bronchoalveolar lavage confirmed the protection exerted by EGF to the alveolar wall and septal capillary endothelium. Furthermore, it was observed that the protection afforded by the treatment with EGF incorporated into vesicles includes improved ventilation capacity expressed in greater arterial $PO_2$ rate, and keeping arterial pH very close to normal. These data are shown in Table 16.

TABLE 16

Results of bronchoalveolar lavage and lung function

| Group | Inflammatory cells per ml | Red blood cells per ml | Total phospholipids per g of lung tissue | Arterial saturation | Arterial pH |
|---|---|---|---|---|---|
| A | $3.0 \times 10^4$ | $2.0 \times 10^3$ | 188.6 µg | 51.8 ± 2.2 | 6.58 ± 0.4 |
| B | $2.2 \times 10^3$ | $5.0 \times 10^2$ | 241.0 µg | 76 ± 8.3 | 7.12 ± 0.1 |
| C | $0.5 \times 10^3$ | — | 1.32 mg | 91.7 ± 5.6 | 7.33 ± 0.2 |

Histological analysis of the lungs from each group showed that EGF treatment, particularly in the group receiving the vesicle formulation protects the lung parenchyma. This is demonstrated by the presence of relative preservation of the alveolus/septum ratio, reduction of the septal wall permeability edema, as well as the presence of hemorrhagic foci and eosinophilic material in the alveolar lumen. Less inflammatory reaction was found in the animals treated with the formulation of vesicle-incorporated EGF, compared to those receiving physiological saline solution. The experiment allows us to infer that intervention with cholesterol:BKC:EGF vesicles, described in Example 4, exerts more intense/prolonged pharmacological effect on the lung parenchyma exposed to known inducers of ALI. The protection conferred covers not only improvement of the structural integrity of the lung, but also presents substantial correction of functional parameters.

Example 20. Compassionate Treatment with EGF Vesicles of a Critically Ill Patient with Adult Respiratory Distress Syndrome (ARDS)

Description of the case: Patient AGJ, male, 75 years old, without pathological medical history, who suffers abdominal trauma progressing to septic shock. ARDS occurs as an evolutionary complication, leading to ventilation difficulty with dyspnea and cyanosis refractory to oxygen therapy, low saturation (11 mm Hg) and blood pH changes. A radiological image shows cotton wool spots in the parenchyma of both lungs. It was decided to start treatment with positive end-expiratory pressure and other routine drugs. In order to protect the lung parenchyma in the acute exudative phase, cholesterol:BKC:EGF vesicles described in Example 4 are administered at a dose of 200 µg equivalents of EGF per liter of medical oxygen, twice daily. The measures allowed a favorable and progressive evolution of the patient to normal, preventing the fibrosing alveolitis phase. On the third day of treatment, positive pressure ventilation could be suspended, and on the fifth day the cotton-like image had been completely cleared.

Example 21. Demonstration of the Therapeutic Efficacy of EGF-Vesicle Use in Patients with Distal Left Ulcerative Colitis This is a cohort of 8 patients with distal ulcerative colitis diagnosis, after several colonoscopies and biopsies were performed. Patients received a special medical diet, as well as pharmacological treatment with azulfidine or sulfasalazine. Because this cohort had remained clinically active for more than 12 months and refractory to all pharmacological interventions, including corticoids, they are evaluated for compassionate treatment by low enema administration of cholesterol:cetrimide:EGF, vesicles described in Example 3. For this, cholesterol:cetrimide:EGF vesicles are administered in physiological saline, at an equivalent EGF concentration of 50 µg/ml, in a volume of 20 ml. The enemas were applied in left lateral decubitus, every night before sleeping time. At 7 days after onset of the enemas associated with other previous medical measures, melenas, pain, and general systemic malaise were eradicated. After 10 days of treatment, a colonoscopy is performed, detecting substantial reduction of mucosal inflammation, healing of most lesions and significant reduction in St. Mark's index. Treatment was discontinued 21 days after onset, when colonoscopies are repeated, confirming the effect of healing and reduction of inflammation brought about by the treatment with enemas containing the cholesterol:cetrimide:EGF vesicles. Biopsies taken from the 8 patients, at 21 days of starting treatment, showed the disappearance of cryptitis.

Example 22. Compassionate Use of EGF Vesicles to Revert Mucosal Lesions Caused by Cancer Chemotherapy Patient QED, male, 32 years old, who developed hemorrhagic mucositis in the bladder and lower parts of the urinary tract, as consequence of cyclophosphamide and busulfan therapy, after bone marrow transplantation. After 72 hours with hematuria and substantial proteinuria (400 mg/24 hours), the patient received, together with general medical support measures, a cystoclysis through which an infusion of physiological saline solution containing cholesterol: CTAB:EGF vesicles, prepared as in Example 2 at equivalent concentration of 150 µg/mL of EGF. At the end of the first 24 hours, only traces of red blood cells were detected in urine and proteinuria of 170 mg/24 hours. Patient IRT, female, 27 years old, develops mucositis of upper parts of the gastrointestinal tract, in the course of polychemotherapy for treatment of non-Hodgkin lymphoma. A full-blown clinical picture, including aphthous manifestations, sialorrhea, even hematemesis, abdominal distension, general malaise, fever and other symptoms appears. The process begins to be managed by pharmacological measures, which included proton pump inhibitors, mucoprotectors, restitution of volemia and analgesic parenteral opioids. Twenty-four hours after onset of the clinical picture, the patient receives oral applications of a saline solution containing cholesterol: cetrimide:EGF vesicles, prepared as in Example 3 at an equivalent concentration of EGF of 50 µg/mL. Using a nasogastric catheter, a volume of 250 ml of this solution was instilled every four hours. Hematemesis ceased after 24 hours of gastric irrigation onset, as well as the distension and acute paresis. Similarly, the need for volume support and other management measures was progressively reduced.

Example 23. Synthesis of β-Sitosterol:CTAB:EGF Vesicles Using Compressed Fluid Technology These vesicles were similarly synthesized to those in Example 2, but in this case, on one hand, a solution of 77.71 mg of β-Sitosterol in 2.88 mL of ethanol and; on the other one, an aqueous solution of 2.83 mg/mL of CTAB and EGF, to the desired concentration, was used. CTAB:β-Sitosterol (1:1) vesicles were obtained with EGF incorporated at a concentration of 5 µM. The results for physical appearance, mean size and Z-potential are shown in Table 17. It can be observed that the vesicle preparation is stable and has a relatively small mean size and PDI. Mean size, particle size distribution and the Z-potential were determined by DLS. Furthermore, similar to the vesicle preparations shown in the previous examples, which comprise in their composition a cationic surfactant of quaternary ammonium type, they have positive Z-potential values much higher than +30 mV, which predicts their high long-term stability. FIG. 3D shows that spheroidal shapes with unilamellar structure predominate, according to the vesicle morphology study performed by cryo-TEM. These vesicles also have features that make them very attractive from a pharmaceutical point of view.

TABLE 17

Physical appearance, mean particle size and Z-potential of the β-Sitosterol:CTAB:EGF vesicles at a given composition.

| Composition (EGF:β-Sitosterol) | Physical appearance | Mean size (nm) (PDI)* | Z-Potencial (mV) (±SD)* |
|---|---|---|---|
| 5 µM:1 M | Disperse opalescent solution | 218.8 (0.277) | +78.6 (±12.0) |

*Nano-ZS (Malvern Instruments, United Kingdom),
PDI—polydispersity index 2309525.1

The invention claimed is:

1. Vesicles comprising epidermal growth factor (EGF), a cationic surfactant selected from the group consisting of cetyltrimethylammonium bromide (CTAB) and tetradecyl methylammonium bromide (cetrimide), and cholesterol wherein the molar ratio of EGF:cationic surfactant:cholesterol is in the range of from 0.137 mM:1 M:1 M to 5.472 mM:1 M:1 M.

2. The vesicles of claim 1, which are characterized by having unilamellar structure and an approximate mean size between 25 and 500 nm.

3. The vesicles of claim 1, wherein the EGF is incorporated into the vesicle bilayer.

4. The vesicles of claim 1, which are obtained by the compressed fluid (CF) technology.

5. Pharmaceutical composition comprising the vesicles of claim 1, and at least one pharmaceutically acceptable excipient.

6. The composition of claim 5, which is formulated for systemic, intralesional, mucosal, topical, transdermal, ophthalmic routes or as an inhaled formulation.

7. A method of treating complex wounds of peripheral soft tissues in a mammal in need thereof, comprising administering a medicament comprising the vesicles of claim 1 to the mammal.

8. The method of claim 7, wherein the complex wound is a diabetic foot ulcer.

9. The method of claim 7, wherein the complex wound is a venous ulcer, a decubitus ulcer or a burn.

10. A method of treating adult respiratory distress in a mammal in need thereof, comprising administering a medicament comprising the vesicles of claim 1 to the mammal.

11. A method of treating digestive tract lesions in a mammal in need thereof, comprising administering a medicament comprising the vesicles of claim 1 to the mammal.

12. The method of claim 11, wherein the digestive tract lesions are mucositis, ulcerative colitis, duodenal ulcers or distal colitis.

13. A method of treating eye lesions in a mammal in need thereof, comprising administering a medicament comprising the vesicles of claim 1 to the mammal.

14. A method of preventing senescence and aging of the skin in a mammal in need thereof, comprising administering a medicament comprising the vesicles of claim 1 to the mammal.

15. The vesicles of claim 2, which are characterized by having unilamellar structure and an approximate mean size between 50 and 300 nm.

16. Vesicles comprising epidermal growth factor (EGF), a cationic surfactant and cholesterol or derivatives thereof, wherein the cationic surfactant is of quaternary ammonium type, wherein the vesicles are produced by a process comprising:
   a) preparing an aqueous solution of EGF and a cationic surfactant,
   b) dissolving cholesterol, or derivatives thereof, in an organic solvent to form an organic solution,
   c) expanding the organic solution with a compressed fluid (CF) to form an expanded organic solution, and
   d) depressurizing the expanded organic solution resulting from stage (c) on the aqueous solution resulting from stage (a),
   wherein vesicles are prepared.

17. Vesicles comprising epidermal growth factor (EGF), benzalkonium chloride (BKC) and cholesterol wherein the molar ratio of EGF:BKC:cholesterol is 0.638 mM: 1 M:1 M.

18. The vesicles of claim 17, which are characterized by having unilamellar structure and an approximate mean size between 25 and 500 nm.

19. The vesicles of claim 17, wherein the EGF is incorporated into the vesicle bilayer.

20. The vesicles of claim 17, which are obtained by the compressed fluid (CF) technology.

21. Pharmaceutical composition comprising the vesicles of claim 17, and at least one pharmaceutically acceptable excipient.

22. The composition of claim 21, which is formulated for systemic, intralesional, mucosal, topical, transdermal, ophthalmic routes or as an inhaled formulation.

23. The vesicles of claim 18, which are characterized by having unilamellar structure and an approximate mean size between 50 and 300 nm.

* * * * *